(12) United States Patent
Xu et al.

(10) Patent No.: US 8,735,561 B2
(45) Date of Patent: May 27, 2014

(54) VIRUS-LIKE PARTICLES OF CAPSID PROTEINS FROM HUMAN PAPILLOMAVIRUS TYPE 16/58/18/6/11 AND THE METHOD FOR PREPARATION AND THE USES THEREOF

(75) Inventors: Xuemei Xu, Beijing (CN); Ting Zhang, Beijing (CN); Yufei Xu, Beijing (CN); Dongsheng Fan, Beijing (CN)

(73) Assignee: Chinese Academy of Medical Sciences, Institute of Basic Medical Sciences, Beijing (CN)

( * ) Notice: Subject to any disclaimer, the term of this patent is extended or adjusted under 35 U.S.C. 154(b) by 1401 days.

(21) Appl. No.: 12/441,393

(22) PCT Filed: Sep. 18, 2007

(86) PCT No.: PCT/CN2007/070715
§ 371 (c)(1),
(2), (4) Date: Jul. 11, 2011

(87) PCT Pub. No.: WO2008/034388
PCT Pub. Date: Mar. 27, 2008

(65) Prior Publication Data
US 2012/0107350 A1  May 3, 2012

(30) Foreign Application Priority Data
Sep. 18, 2006 (CN) .......................... 2006 1 0127387

(51) Int. Cl.
*C12N 15/37* (2006.01)
*C12N 15/85* (2006.01)
*C12N 1/21* (2006.01)
*C12N 15/866* (2006.01)

(52) U.S. Cl.
USPC ................ 536/23.72; 435/320.1; 435/252.33; 435/235.1

(58) Field of Classification Search
None
See application file for complete search history.

(56) References Cited

U.S. PATENT DOCUMENTS 6,066,324 A * 5/2000 Gissmann et al. ......... 424/204.1

OTHER PUBLICATIONS

Harper DM et al. Efficacy of a bivalent L1 virus-like particle vaccine in prevention of infection with human papillomavirus types 16 and 18 in young women: a randomised controlled trial. Lancet. Nov. 13-19, 2004;364(9447):1757-65.*
Kei Kawana et al. Nasal immunization of mice with peptide having a cross-neutralization epitope on minor capsid protein L2 of human papillomavirus type 16 elicit systemic and mucosal antibodies. Vaccine 19 (2001) 1496-1502.*
Genbank: AAQ92369.1.*
Gen Bank: AY383628.1. Synthetic construct HPV18 major capsid protein L1 (L1) gene, complete cds. Published on Oct. 11, 2003.*

* cited by examiner

*Primary Examiner* — Mary E Mosher
*Assistant Examiner* — Nick Zou
(74) *Attorney, Agent, or Firm* — Eagle IP Limited; Jacqueline C. Lui

(57) ABSTRACT

Five optimized genes of capsid L1 protein from human papillomavirus type 16, 58, 18, 6 and 11, which are modified by using insect's preferred codons and so on. Method for modifying those genes to express more highly in insect cells. Virus-like particle's vaccine compositions comprising HPV L1 proteins or their functional relatives produced by using those modified genes. Those optimized genes of L1 can be used to produce HPV 16 VLP, HPV 58VLP, HPV 18VLP, HPV 6 VLP, HPV 11VLP in insect cells. Yields of virus-like particles derived from those optimized HPV L1 genes are high. Mixed multivalent vaccines comprising above optimized HPV L1 genes can be used to prevent and treat multiple HPV infection and diseases related with it.

6 Claims, 29 Drawing Sheets

```
             1                                                  50
HPV_16_L1wt  ATGTCTCTTT GGCTGCCTAG TGAGGCCACT GTCTACTTGC CTCCTGTCCC
HPV_16_L1M   ATGTCCCTGT GGCTGCCCTC CGAGGCCACC GTGTACCTGC CCCCCGTGCC
             51                                                 100
HPV_16_L1wt  AGTATCTAAG GTTGTAAGCA CGGATGAATA TGTTGCACGC ACAAACATAT
HPV_16_L1M   CGTGTCCAAG GTGGTGTCCA CCGACGAGTA CGTGGCTCGC ACCAACATCT
             101                                                150
HPV_16_L1wt  ATTATCATGC AGGAACATCC AGACTACTTG CAGTTGGACA TCCCTATTTT
HPV_16_L1M   ACTACCACGC TGGTACCTCC CGCCTGCTGG CAGTTGGACA TCCCTATTTT
             151                                                200
HPV_16_L1wt  CCTATTAAAA AACCTAACAA TAACAAAATA TTAGTTCCTA AAGTATCAGG
HPV_16_L1M   CCTATTAAAA AACCTAACAA TAACAAAATA TTAGTTCCTA AAGTATCAGG
             201                                                250
HPV_16_L1wt  ATTACAATAC AGGGTATTTA GAATACATTT ACCTGACCCC AATAAGTTTG
HPV_16_L1M   ATTACAATAC AGGGTATTTA GAATACATTT ACCTGACCCC AATAAGTTTG
             251                                                300
HPV_16_L1wt  GTTTTCCTGA CACCTCATTT TATAATCCAG ATACACAGCG GCTGGTTTGG
HPV_16_L1M   GTTTTCCTGA CACCTCATTT TATAATCCAG ATACACAGCG GCTGGTTTGG
             301                                                350
HPV_16_L1wt  GCCTGTGTAG GTGTTGAGGT AGGTCGTGGT CAGCCATTAG GTGTGGGCAT
HPV_16_L1M   GCCTGTGTAG GTGTTGAGGT AGGTCGTGGT CAGCCATTAG GTGTGGGCAT
             351                                                400
HPV_16_L1wt  TAGTGGCCAT CCTTTATTAA ATAAATTGGA TGACACAGAA AATGCTAGTG
HPV_16_L1M   TAGTGGCCAT CCTTTATTAA ATAAATTGGA TGACACAGAA AATGCTAGTG
             401                                                450
HPV_16_L1wt  CTTATGCAGC AAATGCAGGT GTGGATAATA GAGAATGTAT ATCTATGGAT
HPV_16_L1M   CTTATGCAGC AAATGCAGGT GTGGATAATA GAGAATGTAT ATCTATGGAT
             451                                                500
HPV_16_L1wt  TACAAACAAA CACAATTGTG TTTAATTGGT TGCAAACCAC CTATAGGGGA
HPV_16_L1M   TACAAACAAA CACAATTGTG TTTAATTGGT TGCAAACCAC CTATAGGGGA
             501                                                550
HPV_16_L1wt  ACACTGGGGC AAAGGATCCC CATGTACCAA TGTTGCAGTA AATCCAGGTG
HPV_16_L1M   ACACTGGGGC AAAGGATCCC CATGTACCAA TGTTGCAGTA AATCCAGGTG
             551                                                600
HPV_16_L1wt  ATTGTCCACC ATTAGAGTTA ATAAACACAG TTATTCAGGA TGGTGATATG
HPV_16_L1M   ATTGTCCACC ATTAGAGTTA ATAAACACAG TTATTCAGGA TGGTGATATG
```

Fig.1(A)

```
                        601                                              650
HPV_16_L1wt   GTTGACACTG GCTTTGGTGC TATGGACTTT ACTACATTAC AGGCTAACAA
HPV_16_L1M    GTTGATACTG GCTTTGGTGC TATGGACTTT ACTACATTAC AGGCTAACAA
                        651                                              700
HPV_16_L1wt   AAGTGAAGTT CCACTGGATA TTTGTACATC TATTTGCAAA TATCCAGATT
HPV_16_L1M    AAGTGAAGTT CCACTGGATA TTTGTACATC TATTTGCAAA TATCCAGATT
                        701                                              750
HPV_16_L1wt   ATATTAAAAT GGTGTCAGAA CCATATGGCG ACAGCTTATT TTTTTATTTA
HPV_16_L1M    ATATTAAAAT GGTGTCAGAA CCATATGGCG ACAGCTTATT TTTTTATTTA
                        751                                              800
HPV_16_L1wt   CGAAGGGAAC AAATGTTTGT TAGACATTTA TTTAATAGGG CTGGTGCTGT
HPV_16_L1M    CGAAGGGAAC AAATGTTTGT TAGACATTTA TTTAATAGGG CTGGTGCTGT
                        801                                              850
HPV_16_L1wt   TGGTGAAAAT GTACCAGACG ATTTATACAT TAAAGGCTCT GGGTCTACTG
HPV_16_L1M    TGGTGAAAAT GTACCAGACG ATTTATACAT TAAAGGCTCT GGGTCTACTG
                        851                                              900
HPV_16_L1wt   CAAATTTAGC CAGTTCAAAT TATTTTCCTA CACCTAGTGG TTCTATGGTT
HPV_16_L1M    CAAATTTAGC CAGTTCAAAT TATTTTCCTA CACCTAGTGG TTCTATGGTT
                        901                                              950
HPV_16_L1wt   ACCTCTGATG CCCAAATATT CAATAAACCT TATTGGTTAC AACGAGCACA
HPV_16_L1M    ACCTCTGATG CCCAAATATT CAATAAACCT TATTGGTTAC AACGAGCACA
                        951                                             1000
HPV_16_L1wt   GGGCCACAAT AATGGCATTT GTTGGGGTAA CCAACTATTT GTTACTGTTG
HPV_16_L1M    GGGCCACAAT AATGGCATTT GTTGGGGTAA CCAACTATTT GTTACTGTTG
                       1001                                             1050
HPV_16_L1wt   TTGATACTAC ACGCAGTACA AATATGTCAT TATGTGCTGC CATATCTACT
HPV_16_L1M    TTGATACTAC ACGCAGTACA AATATGTCTT TATGTGCTGC CATATCTACT
                       1051                                             1100
HPV_16_L1wt   TCAGAAACTA CATATAAAAA TACTAACTTT AAGGAGTACC TACGACATGG
HPV_16_L1M    TCAGAAACTA CATATAAAAA TACTAACTTT AAGGAGTACC TACGACATGG
                       1101                                             1150
HPV_16_L1wt   GGAGGAATAT GATTTACAGT TTATTTTTCA ACTGTGCAAA ATAACCTTAA
HPV_16_L1M    GGAGGAATAT GATTTACAGT TTATTTTTCA ACTGTGCAAA ATAACCTTAA
                       1151                                             1200
HPV_16_L1wt   CTGCAGACGT TATGACATAC ATACATTCTA TGAATTCCAC TATTTTGGAG
HPV_16_L1M    CTGCAGACGT TATGACATAC ATACATTCTA TGAATTCTAC TATTTTGGAG
```

Fig.1(B)

```
              1201                                              1250
HPV_16_L1wt   GACTGGAATT TTGGTCTACA ACCTCCCCCA GGAGGCACAC TAGAAGATAC
HPV_16_L1M    GACTGGAATT TTGGTCTACA ACCTCCCCCA GGAGGCACAC TAGAAGATAC
              1251                                              1300
HPV_16_L1wt   TTATAGGTTT GTAACATCCC AGGCAATTGC TTGTCAAAAA CATACACCTC
HPV_16_L1M    TTATAGGTTT GTAACATCCC AGGCAATTGC TTGTCAAAAA CATACACCTC
              1301                                              1350
HPV_16_L1wt   CAGCACCTAA AGAAGATCCC CTTAAAAAAT ACACTTTTTG GGAAGTAAAT
HPV_16_L1M    CAGCACCTAA AGAAGATCCC CTTAAAAAAT ACACTTTTTG GGAAGTAAAT
              1351                                              1400
HPV_16_L1wt   TTAAAGGAAA AGTTTTCTGC AGACCTAGAT CAGTTTCCTT TAGGACGCAA
HPV_16_L1M    TTAAAGGAAA AGTTTTCTGC AGACCTAGAT CAGTTTCCTT TAGGACGCAA
              1401                                              1450
HPV_16_L1wt   ATTTTTACTA CAAGCAGGAT TGAAGGCCAA ACCAAAATTT ACATTAGGAA
HPV_16_L1M    ATTTTTACTA CAAGCAGGAT TGAAGGCCAA ACCAAAATTT ACATTAGGAA
              1451                                              1500
HPV_16_L1wt   AACGAAAAGC TACACCCACC ACCTCATCTA CCTCTACAAC TGCTAAACGC
HPV_16_L1M    AACGAAAAGC TACACCCACC ACCTCATCTA CCTCTACAAC TGCTAAACGC
              1501            1518
HPV_16_L1wt   AAAAAACGTA AGCTGTAA
HPV_16_L1M    AAAAAACGTA AGCTGTAA
```

Fig.1(C)

Fig. 1. Sequence alignment between wild type and modified HPV 16 L1 genes

```
                    1                                                  50
HPV_58_L1M   ATGAGTGTCT GGAGACCCTC CGAAGCAACC GTCTATCTCC CACCCGTCCC
HPV_58_L1wt  ATGTCCGTGT GGCGGCCTAG TGAGGCCACT GTGTACCTGC CTCCTGTGCC
                   51                                                 100
HPV_58_L1M   CGTCAGCAAA GTCGTGTCAA CCGACGAGTA CGTCAGCAGG ACCTCAATCT
HPV_58_L1wt  TGTGTCTAAG GTTGTAAGCA CTGATGAATA TGTGTCACGC ACAAGCATTT
                  101                                                 150
HPV_58_L1M   ACTACTACGC TGGTTCCAGT CGCTTGCTCG CCGTCGGCAA CCCCTACTTC
HPV_58_L1wt  ATTATTATGC TGGCAGTTCC AGACTTTTGG CTGTTGGCAA TCCATATTTT
                  151                                                 200
HPV_58_L1M   AGTATTAAGT CCCCAAACAA CAACAAGAAG GTGCTGGTCC CAAAAGTGAG
HPV_58_L1wt  TCCATCAAAA GTCCCAATAA CAATAAAAAA GTATTAGTTC CAAGGTATC
                  201                                                 250
HPV_58_L1M   CGGCCTGCAA TACCGCGTGT TCCGCGTCAG GCTGCCCGAC CCAAACAAGT
HPV_58_L1wt  AGGCTTACAG TATAGGGTCT TTAGGGTGCG TTTACCTGAT CCCAATAAAT
                  251                                                 300
HPV_58_L1M   TCGGCTTCCC CGACACCAGC TTCTACAATC CCGACACCCA GAGGCTCGTG
HPV_58_L1wt  TTGGTTTTCC TGATACATCT TTTTATAACC CTGATACACA ACGTTTGGTC
                  301                                                 350
HPV_58_L1M   TGGGCCTGCG TGGGCTTGGA GATCGGCCGC GGCCAACCAC TCGGCGTCGG
HPV_58_L1wt  TGGGCATGTG TAGGCCTTGA AATAGGTAGG GGACAGCCAT GGGTGTTGG
                  351                                                 400
HPV_58_L1M   CGTGTCCGGC CACCCCTACC TGAACAAGTT CGACGATACC GAGACATCCA
HPV_58_L1wt  CGTAAGTGGT CATCCTTATT TAAATAAATT TGATGACACT GAAACCAGTA
                  401                                                 450
HPV_58_L1M   ATCGCTACCC AGCCCAACCC GGCAGCGACA ATCGCGAGTG TCTGAGCATG
HPV_58_L1wt  ACAGATATCC CGCACAGCCA GGGTCTGATA ACAGGGAATG CTTATCTATG
                  451                                                 500
HPV_58_L1M   GACTACAAGC AGACCCAGCT GTGCCTGATC GGCTGCAAGC CCCCAACCGG
HPV_58_L1wt  GATTATAAAC AAACACAATT ATGTTTAATT GGCTGTAAAC CTCCCACTGG
                  501                                                 550
HPV_58_L1M   TGAACACTGG GGCAAGGGCG TCGCTTGCAA CAACAACGCC GCCGCCACCG
HPV_58_L1wt  TGAGCATTGG GGTAAAGGTG TTGCCTGTAA CAATAATGCA GCTGCTACTG
                  551                                                 600
HPV_58_L1M   ACTGCCCACC CCTCGAGTTG TTCAACAGCA TCATCGAAGA CGGCGATATG
HPV_58_L1wt  ATTGTCCTCC ATTGGAACTT TTAATTCTA TTATTGAGGA TGGTGACATG
```

Fig.2(A)

|          |     | 601        |            |            |            |            |
|----------|-----|------------|------------|------------|------------|------------|
|          |     |            |            |            |            | 650        |
| HPV_58_L1M |   | GTGGACACCG | GCTTCGGCTG | TATGGATTTC | GGCACCCTCC | AAGCCAACAA |
| HPV_58_L1wt |  | GTAGATACAG | GGTTTGGATG | CATGGACTTT | GGTACATTGC | AGGCTAATAA |
|          |     | 651        |            |            |            | 700        |
| HPV_58_L1M |   | GTCCGACGTC | CCCATCGACA | TCTGCAATTC | CACCTGTAAG | TACCCCGACT |
| HPV_58_L1wt |  | AAGTGATGTG | CCTATTGATA | TTTGTAACAG | TACATGCAAA | TATCCAGATT |
|          |     | 701        |            |            |            | 750        |
| HPV_58_L1M |   | ACCTGAAGAT | GGCATCCGAG | CCCTACGGCG | ACAGCCTCTT | CTTCTTCCTC |
| HPV_58_L1wt |  | ATTTAAAAAT | GGCCAGTGAA | CCTTATGGGG | ATAGTTTGTT | CTTTTTTCTT |
|          |     | 751        |            |            |            | 800        |
| HPV_58_L1M |   | CGCAGGGAAC | AAATGTTCGT | CCGCCATTTC | TTCAACCGCG | CCGGCAAGTT |
| HPV_58_L1wt |  | AGACGTGAGC | AGATGTTTGT | TAGACACTTT | TTTAATAGGG | CTGGAAAACT |
|          |     | 801        |            |            |            | 850        |
| HPV_58_L1M |   | GGGCGAAGCC | GTGCCCGACG | ATTTGTACAT | CAAGGGCAGT | GGCAACACCG |
| HPV_58_L1wt |  | TGGCGAGGCT | GTCCCGGATG | ACCTTTATAT | TAAAGGGTCC | GGTAATACTG |
|          |     | 851        |            |            |            | 900        |
| HPV_58_L1M |   | CCGTCATTCA | GTCCTCCGCA | TTCTTCCCAA | CCCCCTCCGG | CAGCATCGTC |
| HPV_58_L1wt |  | CAGTTATCCA | AAGTAGTGCA | TTTTTTCCAA | CTCCTAGTGG | CTCTATAGTT |
|          |     | 901        |            |            |            | 950        |
| HPV_58_L1M |   | ACAAGCGAGA | GCCAGCTGTT | CAACAAGCCC | TACTGGTTGC | AAAGGGCCCA |
| HPV_58_L1wt |  | ACCTCAGAAT | CACAATTATT | TAATAAGCCT | TATTGGCTAC | AGCGTGCACA |
|          |     | 951        |            |            |            | 1000       |
| HPV_58_L1M |   | GGGCCACAAT | AACGGCATCT | GTTGGGGCAA | CCAACTGTTC | GTCACAGTCG |
| HPV_58_L1wt |  | AGGTCATAAC | AATGGCATTT | GCTGGGGCAA | TCAGTTATTT | GTTACCGTGG |
|          |     | 1001       |            |            |            | 1050       |
| HPV_58_L1M |   | TCGACACAAC | CAGGTCAACC | AACATGACCC | TGTGTACCGA | GGTGACCAAG |
| HPV_58_L1wt |  | TTGATACCAC | TCGTAGCACT | AATATGACAT | TATGCACTGA | AGTAACTAAG |
|          |     | 1051       |            |            |            | 1100       |
| HPV_58_L1M |   | GAGGGCACCT | ACAAGAACGA | CAACTTCAAA | GAGTACGTGA | GGCACGTCGA |
| HPV_58_L1wt |  | GAAGGTACAT | ATAAAAATGA | TAATTTTAAG | GAATATGTAC | GTCATGTTGA |
|          |     | 1101       |            |            |            | 1150       |
| HPV_58_L1M |   | GGAGTACGAT | CTGCAATTCG | TCTTCCAATT | GTGTAAGATC | ACCTTGACCG |
| HPV_58_L1wt |  | AGAATATGAC | TTACAGTTTG | TTTTTCAGCT | TTGCAAAATT | ACACTAACTG |
|          |     | 1151       |            |            |            | 1200       |
| HPV_58_L1M |   | CCGAAATCAT | GACCTACATC | CACACCATGG | ACAGTAACAT | CCTCGAAGAT |
| HPV_58_L1wt |  | CAGAGATAAT | GACATATATA | CATACTATGG | ATTCCAATAT | TTTGGAGGAC |

Fig.2(B)

```
              1201                                              1250
HPV_58_L1M    TGGCAGTTCG GCCTGACCCC CCCACCCAGC GCATCCCTGC AAGATACCTA
HPV_58_L1wt   TGGCAATTTG GTTTAACACC TCCTCCGTCT GCCAGTTTAC AGGACACATA
              1251                                              1300
HPV_58_L1M    CCGCTTCGTC ACAAGTCAAG CCATCACCTG TCAGAAGACC GCTCCACCCA
HPV_58_L1wt   TAGATTTGTT ACCTCCCAGG CTATTACTTG CCAAAAAACA GCACCCCCTA
              1301                                              1350
HPV_58_L1M    AGGAGAAAGA GGACCCCCTG AACAAGTACA CCTTCTGGGA AGTCAATCTG
HPV_58_L1wt   AAGAAAAGGA AGATCCATTA AATAAATATA CTTTTTGGGA GGTTAACTTA
              1351                                              1400
HPV_58_L1M    AAAGAGAAAT TCAGCGCCGA CTTGGACCAA TTCCCACTCG GCAGGAAGTT
HPV_58_L1wt   AAGGAAAAGT TTTCTGCAGA TCTAGATCAG TTTCCTTTGG GACGAAAGTT
              1401                                              1450
HPV_58_L1M    CCTGCTGCAG AGCGGCTTGT AAT....... .......... ..........
HPV_58_L1wt   TTTATTACAA TCAGGCCTTA AAGCAAAGCC CAGACTAAAA CGTTCGGCCC
              1451                                  1497
HPV_58_L1M    .......... .......... .......... .......... .......
HPV_58_L1wt   CTACTACCCG TGCACCATCC ACCAAACGCA AAAAGGTTAA AAAATAA
```

Fig.2(C)

Fig. 2. Sequence alignment between wild type

```
             1                                                50
HPV_18_L1wt  ATGGCTTTGT GGCGGCCTAG TGACAATACC GTATATCTTC CACCTCCTTC
 HPV_18_L1M  ATGGCTCTCT GGAGACCCTC CGATAACACA GTGTACTTGC CCCCCCCCAG
             51                                              100
HPV_18_L1wt  TGTGGCAAGA GTTGTAAATA CCGATGATTA TGTGACTCCC ACAAGCATAT
 HPV_18_L1M  CGTCGCCCGC GTCGTGAACA CAGACGACTA CGTCACCAGG ACCTCAATCT
             101                                             150
HPV_18_L1wt  TTTATCATGC TGGCAGCTCT AGATTATTAA CTGTTGGTAA TCCATATTTT
 HPV_18_L1M  TCTACCACGC CGGTTCAAGC CGCCTGCTGA CCGTCGGCAA CCCCTACTTC
             151                                             200
HPV_18_L1wt  AGGGTTCCTG CAGGTGGTGG CAATAAGCAG GATATTCCTA AGGTTTCTGC
 HPV_18_L1M  CGCGTCCCCG CCGGTGGCGG TAACAAACAA GACATCCCCA AAGTCAGCGC
             201                                             250
HPV_18_L1wt  ATACCAATAT AGAGTATTTA GGGTGCAGTT ACCTGACCCA AATAAATTTG
 HPV_18_L1M  CTATCAGTAC CGCGTGTTCC GCGTCCAACT GCCCGATCCC AACAAGTTCG
             251                                             300
HPV_18_L1wt  GTTTACCTGA TACTAGTATT TATAATCCTG AAACACAACG TTTAGTGTGG
 HPV_18_L1M  GCCTGCCCGA CACCTCCATC TACAACCCCG AGACCCAGAG GCTGGTCTGG
             301                                             350
HPV_18_L1wt  GCCTGTGCTG GAGTGGAAAT TGGCCGTGGT CAGCCTTTAG GTGTTGGCCT
 HPV_18_L1M  GCATGCGCCG GCGTCGAGAT CGGTAGGGGC CAACCCCTGG GCGTCGGTTT
             351                                             400
HPV_18_L1wt  TAGTGGGCAT CCATTTTATA ATAAATTAGA TGACACTGAA AGTTCCCATG
 HPV_18_L1M  GTCCGGCCAC CCCTTCTACA ACAAGCTGGA CGATACCGAG TCCTCCCACG
             401                                             450
HPV_18_L1wt  CCGCCACGTC TAATGTTTCT GAGGACGTTA GGGACAATGT GTCTGTAGAT
 HPV_18_L1M  CAGCAACCAG CAACGTCAGC GAAGATGTCC GCGATAACGT CAGCGTGGAC
             451                                             500
HPV_18_L1wt  TATAAGCAGA CACAGTTATG TATTTTGGGC TGTGCCCCTG CTATTGGGGA
 HPV_18_L1M  TACAAACAAA CCCAACTGTG CATCCTCGGT TGCGCACCCG CCATCGGCGA
             501                                             550
HPV_18_L1wt  ACACTGGGCT AAAGGCACTG CTTGTAAATC GCGTCCTTTA TCACAGGGCG
 HPV_18_L1M  GCATTGGGCC AAGGGTACCG CCTGCAAGAG CAGGCCCCTG AGCCAAGGTG
             551                                             600
HPV_18_L1wt  ATTGCCCCCC TTTAGAACTT AAAAACACAG TTTTGGAAGA TGGTGATATG
 HPV_18_L1M  ACTGTCCACC CCTGGAGTTG AAGAATACCG TCCTCGAGGA CGGCGACATG
```

Fig.3(A)

```
              601                                                650
HPV_18_L1wt   GTAGATACTG GATATGGTGC CATGGACTTT AGTACATTGC AAGATACTAA
HPV_18_L1M    GTGGACACCG GCTACGGCGC AATGGATTTC TCCACCCTGC AGGACACCAA
              651                                                700
HPV_18_L1wt   ATGTGAGGTA CCATTGGATA TTTGTCAGTC TATTTGTAAA TATCCTGATT
HPV_18_L1M    GTGCGAAGTG CCCCTCGACA TCTGCCAAAG CATCTGCAAG TACCCCGACT
              701                                                750
HPV_18_L1wt   ATTTACAAAT GTCTGCAGAT CCTTATGGGG ATTCCATGTT TTTTTGCTTA
HPV_18_L1M    ACCTGCAGAT GAGCGCCGAC CCCTACGGCG ACTCCATGTT CTTCTGTCTG
              751                                                800
HPV_18_L1wt   CGGCGTGAGC AGCTTTTTGC TAGGCATTTT TGGAATAGAG CAGGTACTAT
HPV_18_L1M    AGAAGGGAAC AATTGTTCGC CGCCACTTC TGGAACCGCG CCGGCACCAT
              801                                                850
HPV_18_L1wt   GGGTGACACT GTGCCTCAAT CCTTATATAT TAAAGGCACA GGTATGCCTG
HPV_18_L1M    GGGCGATACC GTCCCCCAGT CCCTGTACAT CAAGGGTACC GGCATGAGGG
              851                                                900
HPV_18_L1wt   CTTCACCTGG CAGCTGTGTG TATTCTCCCT CTCCAAGTGG CTCTATTGTT
HPV_18_L1M    CCAGCCCCGG TTCATGCGTC TACAGCCCAA GCCCCTCCGG TAGCATCGTC
              901                                                950
HPV_18_L1wt   ACCTCTGACT CCCAGTTGTT TAATAAACCA TATTGGTTAC ATAAGGCACA
HPV_18_L1M    ACAAGCGATT CCCAACTCTT CAACAAGCCC TACTGGCTGC ACAAAGCCCA
              951                                                1000
HPV_18_L1wt   GGGTCATAAC AATGGTGTTT GCTGGCATAA TCAATTATTT GTTACTGTGG
HPV_18_L1M    AGGCCACAAT AACGGCGTCT GTTGGCACAA CCAGCTGTTC GTCACCGTCG
              1001                                               1050
HPV_18_L1wt   TAGATACCAC TCCCAGTACC AATTTAACAA TATGTGCTTC TACACAGTCT
HPV_18_L1M    TGGACACAAC CAGGTCCACA AACCTGACCA TCTGCGCCAG CACCCAAAGC
              1051                                               1100
HPV_18_L1wt   CCTGTACCTG GCAATATGA TGCTACCAAA TTTAAGCAGT ATAGCAGACA
HPV_18_L1M    CCCGTGCCCG GCCAGTACGA CGCCACAAAG TTCAAACAAT ACTCACGCCA
              1101                                               1150
HPV_18_L1wt   TGTTGAGGAA TATGATTTGC AGTTTATTTT TCAGTTGTGT ACTATTACTT
HPV_18_L1M    CGTCGAAGAG TACGACCTCC AATTCATCTT CCAACTCTGC ACCATCACCC
              1151                                               1200
HPV_18_L1wt   TAACTGCAGA TGTTATGTCC TATATTCATA GTATGAATAG CAGTATTTTA
HPV_18_L1M    TGACCGCCGA CGTCATGTCC TACATCCACT CCATGAACTC ATCCATCCTG
```

Fig.3(B)

```
              1201                                            1250
HPV_18_L1wt   GAGGATTGGA ACTTTGGTGT TCCCCCCCCC CCAACTACTA GTTTGGTGGA
HPV_18_L1M    GAAGACTGGA ATTTCGGCGT CCCACCACCC CCCACCACCT CCCTCGTCGA
              1251                                            1300
HPV_18_L1wt   TACATATCGT TTTGTACAAT CTGTTGCTAT TACCTGTCAA AAGGATGCTG
HPV_18_L1M    CACCTACAGG TTCGTGCAGA GCGTCGCCAT CACATGCCAG AAAGACGCCG
              1301                                            1350
HPV_18_L1wt   CACCGGCTGA AAATAAGGAT CCCTATGATA AGTTAAAGTT TTGGAATGTG
HPV_18_L1M    CCCCCGCCGA GAACAAAGAC CCATACGACA AACTGAAATT CTGGAACGTC
              1351                                            1400
HPV_18_L1wt   GATTTAAAGG AAAAGTTTTC TTTAGACTTA GATCAATATC CCCTTGGACG
HPV_18_L1M    GACCTGAAAG AGAAATTCAG CCTGGATCTG GACCAGTACC CATTGGGCAG
              1401                                            1450
HPV_18_L1wt   TAAAATTTTTG GTTCAGGCTG GATTGCGTCG CAAGCCCACC ATAGGCCCTC
HPV_18_L1M    GAAGTTCCTC GTCCAGGCGG GTCTCTAAT. .......... ..........
              1451                                            1500
HPV_18_L1wt   GCAAACGTTC TGCTCCATCT GCCACTACGT CTTCTAAACC TGCCAAGCGT
HPV_18_L1M    .......... .......... .......... .......... ..........
              1501                 1524
HPV_18_L1wt   GTGCGTGTAC GTGCCAGGAA GTAA
```

Fig.3(C)

Fig. 3. Sequence alignment between wild type and modified HPV 18 L1 genes

```
           1                                                     50
HPV_6_L1M  ATGTGGCGTC CCTCAGATTC AACCGTGTAC GTCCCCCCCC CTAATCCCGT
HPV_6_L1wt ATGTGGCGGC CTAGCGACAG CACAGTATAT GTGCCTCCTC CTAACCCTGT
           51                                                   100
HPV_6_L1M  GTCCAAAGTC GTCGCTACCG ACGCCTACGT CACCAGGACA AATATCTTCT
HPV_6_L1wt ATCCAAAGTT GTTGCCACGG ATGCTTATGT TACTCGCACC AACATATTTT
           101                                                  150
HPV_6_L1M  ACCACGCTTC ATCCAGCCGC TTGTTGGCCG TCGGCCACCC CTACTTCAGC
HPV_6_L1wt ATCATGCCAG CAGTTCTAGA CTTCTTGCAG TGGGACATCC TTATTTTTCC
           151                                                  200
HPV_6_L1M  ATTAAGCGCG CTAATAAGAC CGTCGTGCCC AAAGTCAGCG GCTACCAGTA
HPV_6_L1wt ATAAAACGGG CTAACAAAAC TGTTGTGCCA AAGGTGTCAG GATATCAATA
           201                                                  250
HPV_6_L1M  CCGCGTCTTC AAAGTGGTCC TCCCCGACCC CAATAAATTC GCCCTGCCCG
HPV_6_L1wt CAGGGTATTT AAGGTGGTGT TACCAGATCC TAACAAATTT GCATTGCCTG
           251                                                  300
HPV_6_L1M  ACAGCTCCCT CTTCGATCCT ACCACCCAAA GGCTGGTGTG GGCCTGTACC
HPV_6_L1wt ACTCGTCTCT TTTCGATCCC ACAACACAAC GTTTAGTATG GGCATGCACA
           301                                                  350
HPV_6_L1M  GGCCTCGAAG TGGGTCGCGG CCAGCCCCTG GGTGTCGGCG TCTCCGGCCA
HPV_6_L1wt GGCCTAGAGG TGGGCAGGGG ACAGCCATTA GGTGTGGGTG TAAGTGGACA
           351                                                  400
HPV_6_L1M  CCCCTTCTTG AATAAGTACG ACGACGTGGA GAACTCCGGC TCCGGCGGCA
HPV_6_L1wt TCCTTTCCTA AATAAATATG ATGATGTTGA AAATTCAGGG AGTGGTGGTA
           401                                                  450
HPV_6_L1M  ACCCCGGCCA AGACAACCGC GTCAACGTGG GCATGGACTA CAAGCAGACA
HPV_6_L1wt ACCCTGGACA GGATAACAGG GTTAATGTAG GTATGGATTA TAAACAAACA
           451                                                  500
HPV_6_L1M  CAATTGTGCA TGGTCGGTTG CGCCCCCCCC CTGGGCGAGC ACTGGGGCAA
HPV_6_L1wt CAATTATGCA TGGTTGGATG TGCCCCCCCT TTGGGCGAGC ATTGGGGTAA
           501                                                  550
HPV_6_L1M  AGGCAAGCAG TGCACCAACA CACCTGTGCA GGCTGGCGAT TGTCCTCCCC
HPV_6_L1wt AGGTAAACAG TGTACTAATA CACCTGTACA GGCTGGTGAC TGCCCGCCCT
           551                                                  600
HPV_6_L1M  TCGAGTTGAT CACATCCGTC ATCCAAGACG GCGATATGGT CGACACCGGT
HPV_6_L1wt TAGAACTTAT TACCAGTGTT ATACAGGATG GCGATATGGT TGACACAGGC
```

Fig.4(A)

|         | 601        |            |            |            | 650        |
|---------|------------|------------|------------|------------|------------|
| HPV_6_L1M  | TTCGGCGCCA | TGAACTTCGC | CGATCTGCAG | ACAAACAAGA | GCGACGTCCC |
| HPV_6_L1wt | TTTGGTGCTA | TGAATTTTGC | TGATTTGCAG | ACCAATAAAT | CAGATGTTCC |
|         | 651        |            |            |            | 700        |
| HPV_6_L1M  | TATCGACATC | TGCGGCACCA | CCTGTAAGTA | CCCCGACTAC | CTCCAGATGG |
| HPV_6_L1wt | TATTGACATA | TGTGGCACTA | CATGTAAATA | TCCAGATTAT | TTACAAATGG |
|         | 701        |            |            |            | 750        |
| HPV_6_L1M  | CCGCCGATCC | CTACGGCGAC | CGCCTCTTCT | TCTTCCTCAG | GAAAGAGCAG |
| HPV_6_L1wt | CTGCAGACCC | ATATGGTGAT | AGATTATTTT | TTTTTCTACG | GAAGGAACAA |
|         | 751        |            |            |            | 800        |
| HPV_6_L1M  | ATGTTCGCCC | GCCATTTCTT | CAACCGCGCT | GGCGAGGTCG | GCGAGCCCGT |
| HPV_6_L1wt | ATGTTTGCCA | GACATTTTTT | TAACAGGGCT | GGCGAGGTGG | GGGAACCTGT |
|         | 801        |            |            |            | 850        |
| HPV_6_L1M  | CCCCGACACC | CTCATCATCA | AGGGCTCCGG | TAATCGCACC | AGCGTGGGCT |
| HPV_6_L1wt | GCCTGATACT | CTTATAATTA | AGGGTAGTGG | AAATCGCACG | TCTGTAGGGA |
|         | 851        |            |            |            | 900        |
| HPV_6_L1M  | CCTCCATCTA | CGTGAACACC | CCCTCCGGTA | GCCTCGTCAG | CAGCGAAGCC |
| HPV_6_L1wt | GTAGTATATA | TGTTAACACC | CCGAGCGGCT | CTTTGGTGTC | CTCTGAGGCA |
|         | 901        |            |            |            | 950        |
| HPV_6_L1M  | CAGCTGTTCA | ACAAGCCCTA | CTGGTTGCAG | AAAGCCCAAG | GCCACAATAA |
| HPV_6_L1wt | CAATTGTTTA | ATAAGCCATA | TTGGCTACAA | AAAGCCCAGG | GACATAACAA |
|         | 951        |            |            |            | 1000       |
| HPV_6_L1M  | CGGCATCTGT | TGGGGCAATC | AGCTCTTCGT | CACCGTCGTG | GACACAACCA |
| HPV_6_L1wt | TGGTATTTGT | TGGGGTAATC | AACTGTTTGT | TACTGTGGTA | GATACCACAC |
|         | 1001       |            |            |            | 1050       |
| HPV_6_L1M  | GGTCCACCAA | CATGACCTTG | TGCGCCAGCG | TCACCACCAG | CTCCACCTAC |
| HPV_6_L1wt | GCAGTACCAA | CATGACATTA | TGTGCATCCG | TAACTACATC | TTCCACATAC |
|         | 1051       |            |            |            | 1100       |
| HPV_6_L1M  | ACCAACAGCG | ACTACAAAGA | GTACATGAGG | CACGTCGAAG | AATACGACCT |
| HPV_6_L1wt | ACCAATTCTG | ATTATAAAGA | GTACATGCGT | CATGTGGAAG | AGTATGATTT |
|         | 1101       |            |            |            | 1150       |
| HPV_6_L1M  | GCAATTCATC | TTCCAGCTCT | GCTCAATCAC | CCTGAGCGCC | GAGGTGATGG |
| HPV_6_L1wt | ACAATTTATT | TTTCAATTAT | GTAGCATTAC | ATTGTCTGCT | GAAGTAATGG |
|         | 1151       |            |            |            | 1200       |
| HPV_6_L1M  | CTTACATCCA | TACCATGAAC | CCCAGCGTCC | TCGAAGATTG | GAATTTCGGT |
| HPV_6_L1wt | CCTATATTCA | CACAATGAAT | CCCTCTGTTT | TGGAAGACTG | GAACTTTGGG |

Fig.4(B)

```
              1201                                              1250
HPV_6_L1M    CTGAGCCCCC CCCCCAACGG CACCCTCGAA GACACCTACC GCTACGTGCA
HPV_6_L1wt   TTATCGCCTC CCCCAAATGG TACATTAGAA GATACCTATA GGTATGTGCA
              1251                                             1300
HPV_6_L1M    AAGCCAAGCT ATCACATGCC AAAAGCCTAC CCCCGAGAAG GAGAAGCCAG
HPV_6_L1wt   GTCACAGGCC ATTACCTGTC AAAAGCCCAC TCCTGAAAAG GAGAAGCCAG
              1301                                             1350
HPV_6_L1M    ACCCTTACAA AAACCTGTCC TTCTGGGAAG TCAATCTGAA GGAGAAATTC
HPV_6_L1wt   ATCCCTATAA AAACCTTAGT TTTTGGGAGG TTAATTTAAA AGAAAAGTTT
              1351                                             1400
HPV_6_L1M    AGCTCCGAGC TGGACCAATA CCCTTTGGGC AGGAAATTCC TGCTCCAGTC
HPV_6_L1wt   TCTAGTGAAT TGGATCAGTA TCCTTTGGGA CGCAAGTTTT TGTTACAAAG
              1401                                             1450
HPV_6_L1M    CGGCTACAGG GGCCGATCCA GCATCAGGAC CGGCGTGAAA AGGCCCGCCG
HPV_6_L1wt   TGGATATAGG GGACGGTCCT CTATTCGTAC AGGTGTTAAG CGCCCTGCTG
              1451                                             1500
HPV_6_L1M    TCAGCAAAGC TAGCGCCGCT CCTAAGAGGA AGAGGGCTAA GACAAAGCGT
HPV_6_L1wt   TTTCCAAAGC CTCTGCTGCC CCTAAACGTA AGCGCGCCAA AACTAAAAGG
              1501
HPV_6_L1M    TAAT
HPV_6_L1wt   TAA.
```

Fig.4(C)

Fig. 4. Sequence alignment between wild type and modified HPV 6 L1 genes

```
                     1                                                  50
HPV_11_L1M   ATGTGGCGTC CCTCAGATTC AACCGTGTAC GTCCCCCCCC CTAATCCCGT
HPV_11_L1wt  ATGTGGCGGC CTAGCGACAG CACAGTATAT GTGCCTCCTC CCAACCCTGT
                    51                                                 100
HPV_11_L1M   GTCCAAAGTC GTCGCTACCG ACGCCTACGT CAAGAGGACA AATATCTTCT
HPV_11_L1wt  ATCCAAGGTT GTTGCCACGG ATGCGTATGT TAAACGCACC AACATATTTT
                   101                                                 150
HPV_11_L1M   ACCACGCTTC ATCCAGCCGC TTGTTGGCCG TCGGCCACCC CTACTACAGC
HPV_11_L1wt  ATCACGCCAG CAGTTCTAGA CTCCTTGCTG TGGGACATCC ATATTACTCT
                   151                                                 200
HPV_11_L1M   ATTAAGAAGG TCAATAAGAC CGTCGTGCCC AAAGTCAGCG GCTACCAGTA
HPV_11_L1wt  ATCAAAAAAG TTAACAAAAC AGTTGTACCA AAGGTGTCTG GATATCAATA
                   201                                                 250
HPV_11_L1M   CCGCGTCTTC AAAGTGGTCC TCCCCGACCC CAATAAATTC GCCCTGCCCG
HPV_11_L1wt  TAGAGTGTTT AAGGTAGTGT TGCCAGATCC TAACAAGTTT GCATTACCTG
                   251                                                 300
HPV_11_L1M   ACAGCTCCCT CTTCGATCCT ACCACCCAAA GGCTGGTGTG GGCCTGTACC
HPV_11_L1wt  ATTCATCTCT GTTTGACCCC ACTACACAGC GTTTAGTATG GGCGTGCACA
                   301                                                 350
HPV_11_L1M   GGCCTCGAAG TGGGTCGCGG CCAGCCCCTG GGTGTCGGCG TCTCCGGCCA
HPV_11_L1wt  GGGTTGGAGG TAGGCAGGGG TCAACCTTTA GGCGTTGGTG TTAGTGGGCA
                   351                                                 400
HPV_11_L1M   CCCCCTCTTG AATAAGTACG ACGACGTGGA GAACTCCGGC GGCTACGGCG
HPV_11_L1wt  TCCATTGCTA AACAAATATG ATGATGTAGA AAATAGTGGT GGGTATGGTG
                   401                                                 450
HPV_11_L1M   GCAACCCCGG CCAAGACAAC CGCGTCAACG TGGGCATGGA CTACAAGCAG
HPV_11_L1wt  GTAATCCTGG TCAGGATAAT AGGGTTAATG TAGGTATGGA TTATAAACAA
                   451                                                 500
HPV_11_L1M   ACACAATTGT GCATGGTCGG TTGCGCCCCC CCCCTGGGCG AGCACTGGGG
HPV_11_L1wt  ACCCAGCTAT GTATGGTGGG CTGTGCTCCA CCGTTAGGTG AACATTGGGG
                   501                                                 550
HPV_11_L1M   CAAAGGCACC CAGTGCAGCA ACACAAGCGT GCAGAACGGC GATTGTCCTC
HPV_11_L1wt  TAAGGGTACA CAATGTTCAA ATACCTCTGT ACAAAATGGT GACTGCCCCC
                   551                                                 600
HPV_11_L1M   CCCTCGAGTT GATCACATCC GTCATCCAAG ACGGCGATAT GGTCGACACC
```

Fig.5(A)

HPV_11_L1wt CGTTGGAACT TATTACCAGT GTTATACAGG ATGGGGACAT GGTTGATACA 601 650

HPV_11_L1M GGTTTCGGCG CCATGAACTT CGCCGATCTG CAGACAAACA AGAGCGACGT

HPV_11_L1wt GGCTTTGGTG CTATGAATTT TGCAGACTTA CAAACCAATA AATCGGATGT 651 700

HPV_11_L1M CCCTTTGGAC ATCTGCGGCA CCGTGTGTAA GTACCCCGAC TACCTCCAGA

HPV_11_L1wt TCCCCTTGAT ATTTGTGGAA CTGTCTGCAA ATATCCTGAT TATTTGCAAA 701 750

HPV_11_L1M TGGCCGCCGA TCCCTACGGC GACCGCCTCT TCTTCTACCT CAGGAAAGAG

HPV_11_L1wt TGGCTGCAGA CCCTTATGGT GATAGGTTGT TTTTTTATTT GCGAAAGGAA 751 800

HPV_11_L1M CAGATGTTCG CCCGCCATTT CTTCAACCGC GCTGGCACCG TCGGCGAGCC

HPV_11_L1wt CAAATGTTTG CTAGACACTT TTTTAATAGG GCCGGTACTG TGGGGGAACC 801 850

HPV_11_L1M CGTCCCCGAC GATCTCCTCG TGAAGGGCGG CAACAATCGC AGCAGC.GTG

HPV_11_L1wt TGTGCCTGAT GACCTGTTGG TAAAAGGGGG TAATAATAG. ATCATCTGTA 851 900

HPV_11_L1M GCCTCCTCCA TCTACGTGCA CACCCCCTCC GGTAGCCTCG TCAGCAGCGA

HPV_11_L1wt GCTAGTAGTA TTTATGTACA TACACCTAGT GGCTCATTGG TGTCTTCAGA 901 950

HPV_11_L1M AGCCCAGCTG TTCAACAAGC CCTACTGGTT GCAGAAAGCC CAAGGCCACA

HPV_11_L1wt GGCTCAATTA TTTAATAAAC CATATTGGCT TCAAAAGGCT CAGGGACATA 951 1000

HPV_11_L1M ATAACGGCAT CTGTTGGGGC AATCATCTCT TCGTCACCGT CGTGGACACA

HPV_11_L1wt ACAATGGTAT TTGCTGGGGA AACCACTTGT TTGTTACTGT GGTAGATACC 1001 1050

HPV_11_L1M ACCAGGTCCA CCAACATGAC CTTGTGCGCC AGCGTCAGCA AGAGCGCCAC

HPV_11_L1wt ACACGCAGTA CAAATATGAC ACTATGTGCA TCTGTGTCTA AATCTGCTAC 1051 1100

HPV_11_L1M CTACACCAAC AGCGACTACA AAGAGTACAT GAGGCACGTC GAAGAATTCG

HPV_11_L1wt ATACACTAAT TCAGATTATA AGGAATACAT GCGCCATGTG AAAGAGTTTG 1101 1150

HPV_11_L1M ACCTGCAATT CATCTTCCAG CTCTGCTCAA TCACCCTGAG CGCCGAGGTG

HPV_11_L1wt ATTTACAGTT TATTTTTCAA TTGTGTAGCA TTACATTATC TGCAGAAGTC 1151 1200

HPV_11_L1M ATGGCTTACA TCCATACCAT GAACCCCAGC GTCCTCGAAG ATTGGAATTT

Fig.5(B)

HPV_11_L1wt  ATGGCCTATA TACACACAAT GAATCCTTCT GTTTTGGAGG ACTGGAACTT

Fig.5(C)

Fig. 5. Sequence alignment between wild type and modified HPV 11 L1 genes

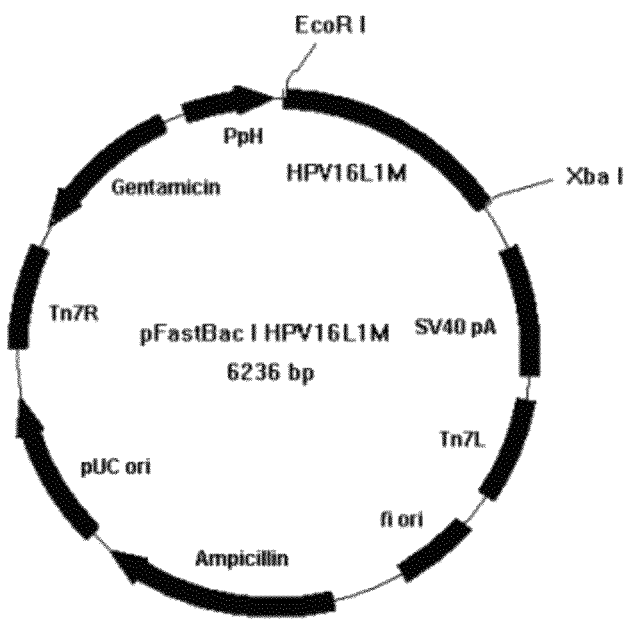
Fig. 6. The map of pFastBacI-HPV 16 L1M construct
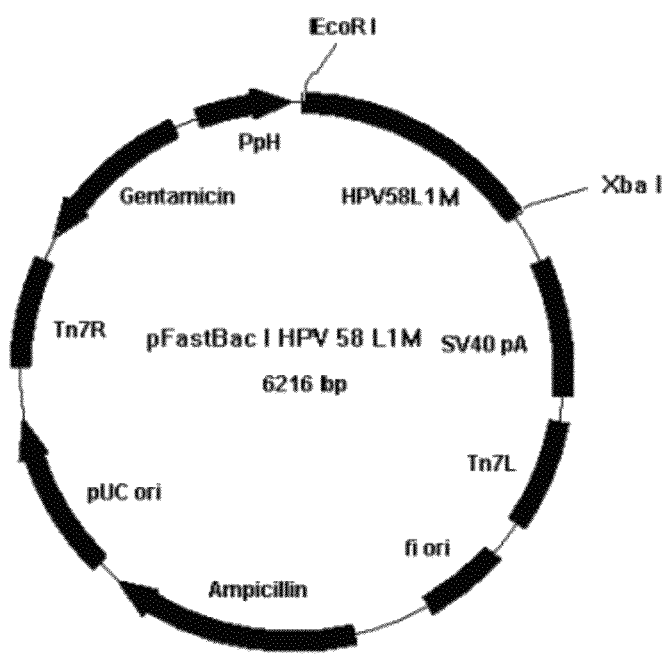
Fig. 7. The map of pFastBacI-HPV 58 L1M construct

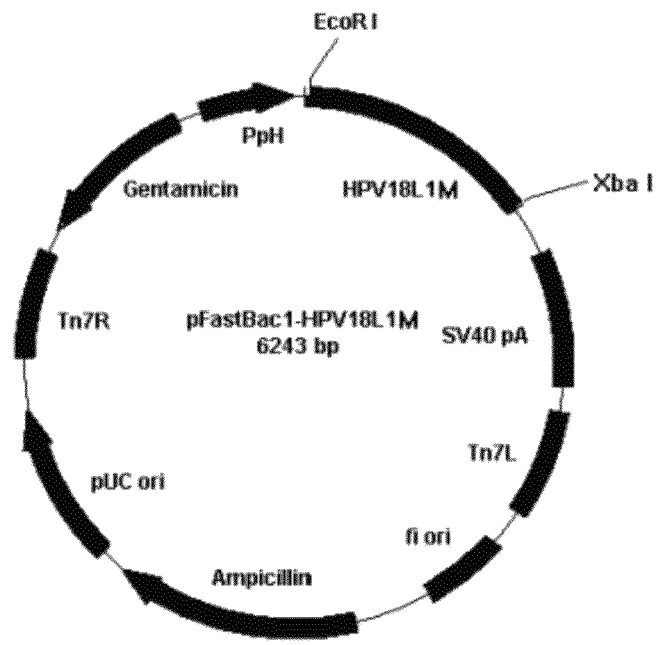
Fig. 8. The map of pFastBacI-HPV 18 L1M construct
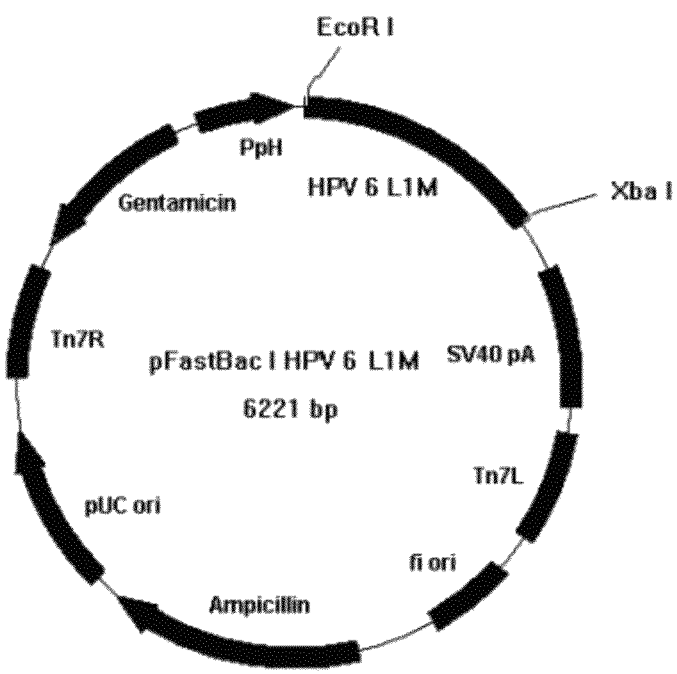
Fig. 9. The map of pFastBacI-HPV 6 L1M construct

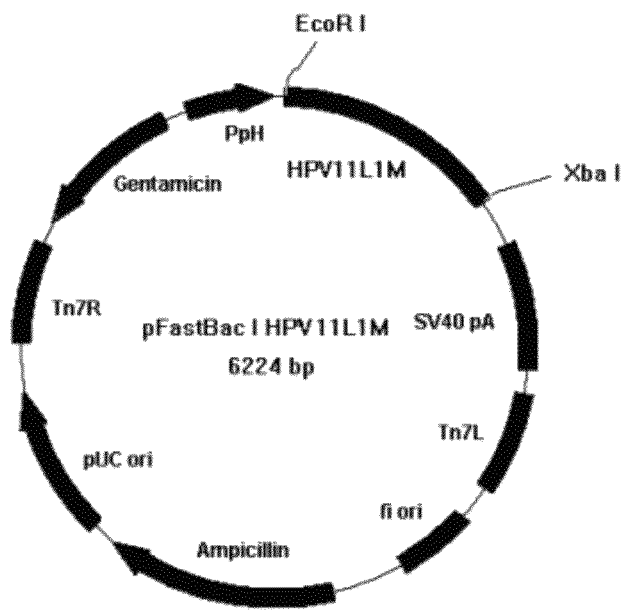
Fig. 10. The map of pFastBacI-HPV 11 L1M construct
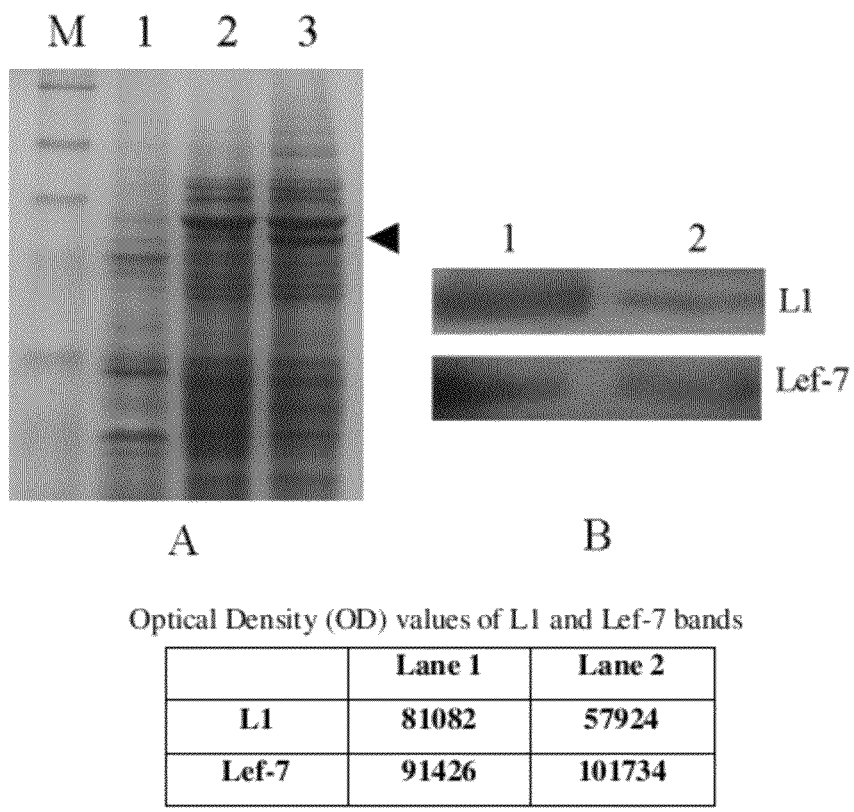
Fig. 11. The expression analysis of modified HPV 11 L1 gene

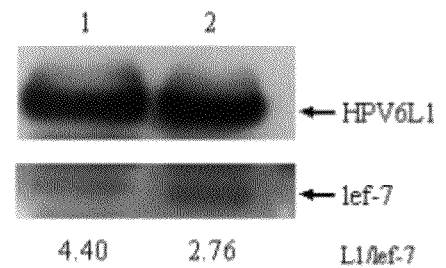
Optical Density (OD) values of L1 and Lef-7 bands
|  | Lane 1 | Lane 2 |
|---|---|---|
| L1 | 435836 | 359264 |
| Lef-7 | 98947 | 130316 |
Fig. 12. The expression analysis of modified HPV 6 L1 gene
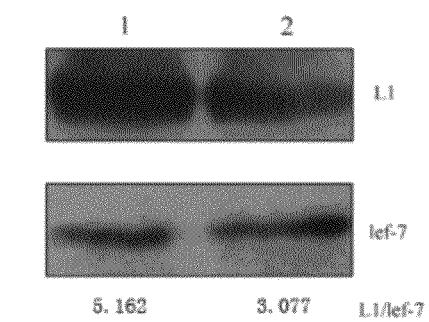
Optical Density (OD) values of L1 and Lef-7 bands
|  | Lane 1 | Lane 2 |
|---|---|---|
| L1 | 298245 | 242562 |
| Lef-7 | 57768 | 78818 |
Fig. 13. The expression analysis of modified HPV 16 L1 gene

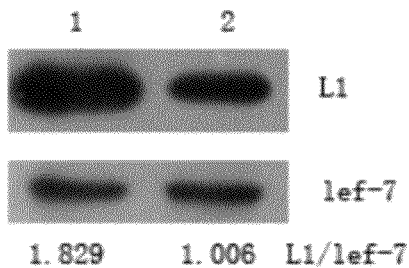
Optical Density (OD) values of L1 and Lef-7 bands
|       | Lane 1 | Lane 2 |
|-------|--------|--------|
| L1    | 273021 | 161159 |
| Lef-7 | 149245 | 160276 |
Fig. 14. The expression analysis of modified HPV 58 L1 gene
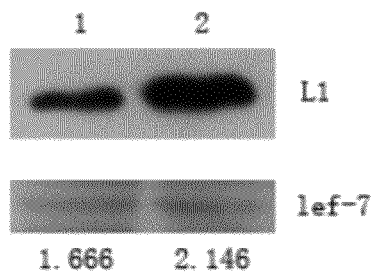
Optical Density (OD) values of L1 and Lef-7 bands
|       | Lane 1 | Lane 2 |
|-------|--------|--------|
| L1    | 127098 | 217837 |
| Lef-7 | 76308  | 101507 |
Fig. 15. The expression analysis of modified HPV 18 L1 gene

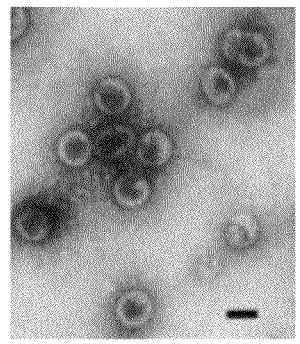
Fig. 16. Transmission electron microscopy assay of HPV 16 L1 VLP. Scale bar = 50 nm
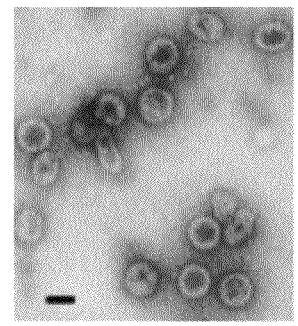
Fig. 17. Transmission electron microscopy assay of HPV 58 L1 VLP. Scale bar = 50 nm
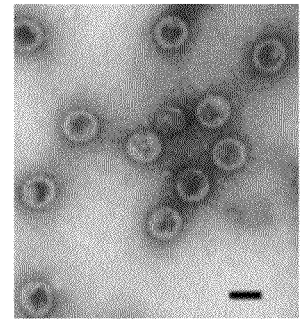
Fig. 18. Transmission electron microscopy assay of HPV 18 L1 VLP. Scale bar = 50 nm

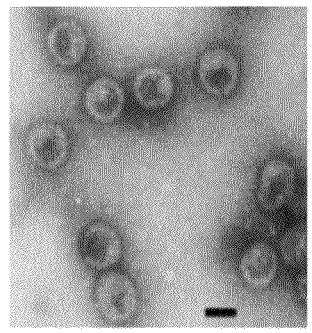
Fig. 19. Transmission electron microscopy assay of HPV 6 L1 VLP. Scale bar = 50 nm
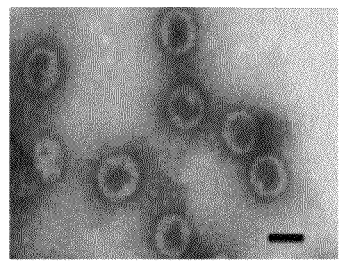
Fig. 20. Transmission electron microscopy assay of HPV 11 L1 VLP. Scale bar = 50 nm
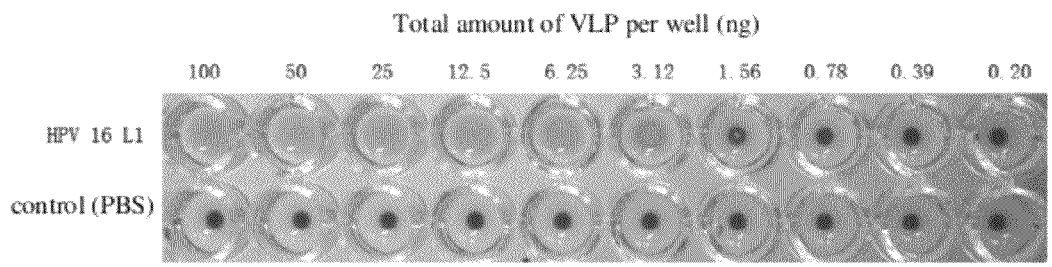
Fig. 21. Hemagglutination assay of HPV 16 L1 VLP

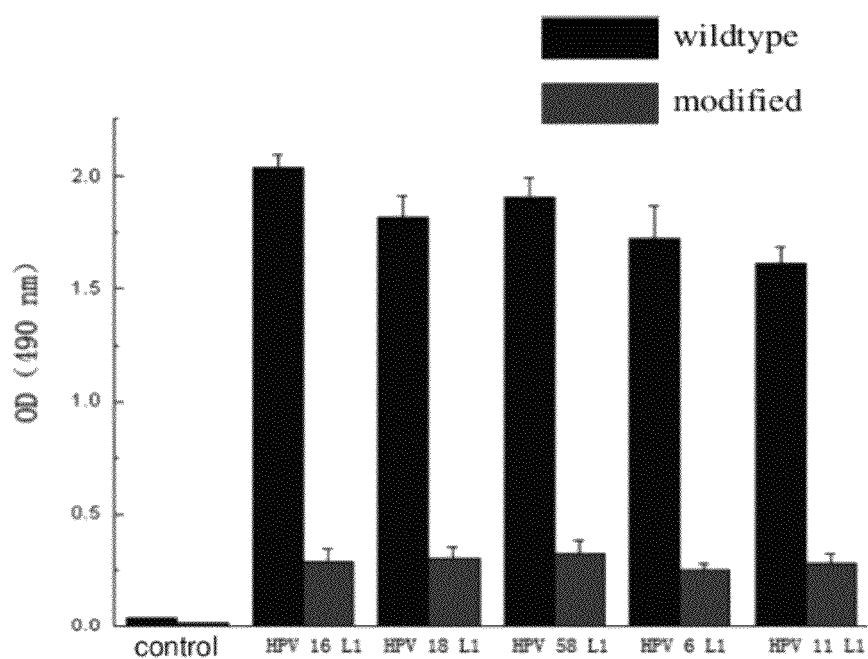
Fig. 22. The conformation-dependent characteristics of serum neutralizing antibodies induced by different types of HPV L1 VLP

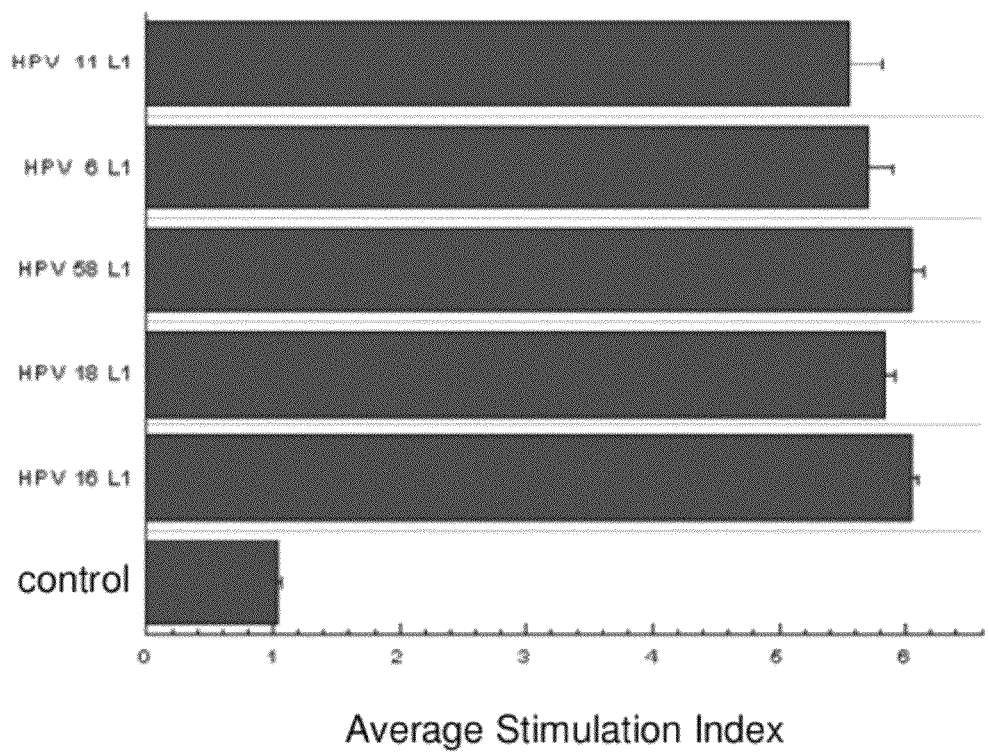
Fig. 23. Splenocytes proliferation assay of different types of HPV L1 VLP

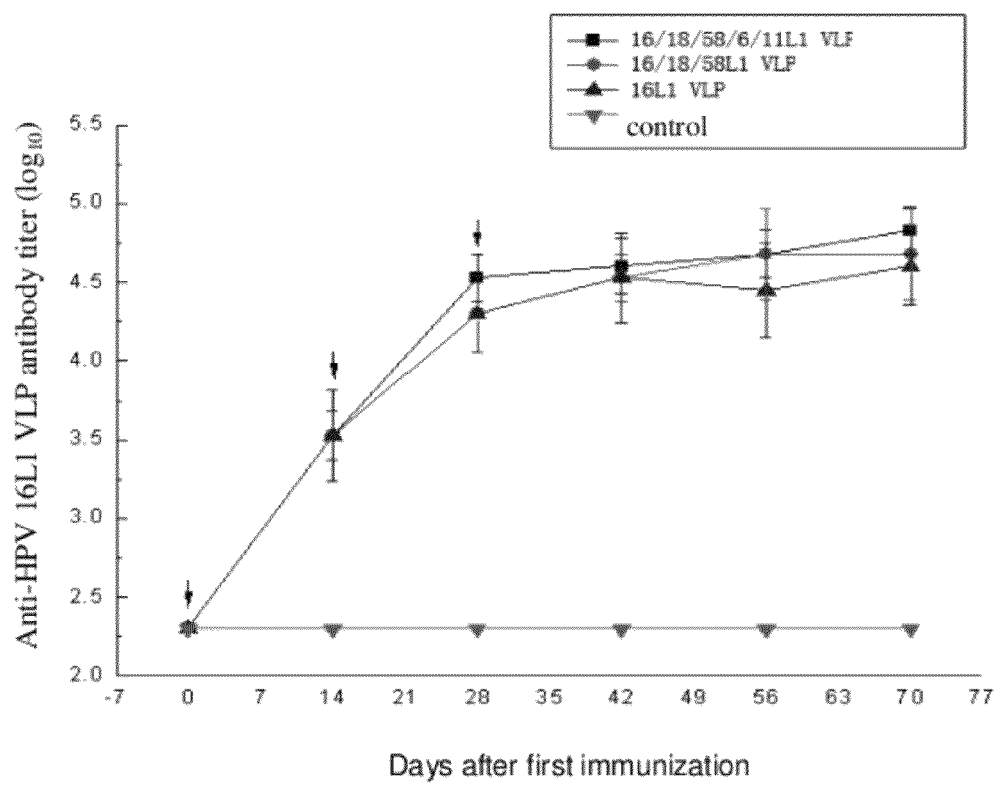
Fig. 24. The titers of HPV 16 L1 VLP-specific neutralizing antibodies

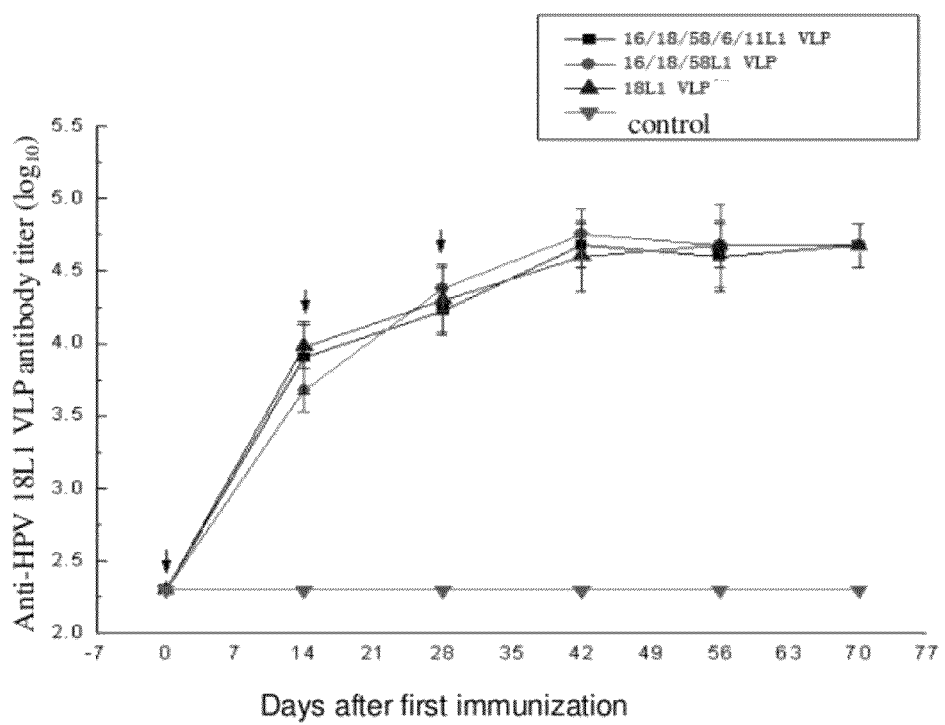
Fig.25. The titers of HPV 18 L1 VLP-specific neutralizing antibodies

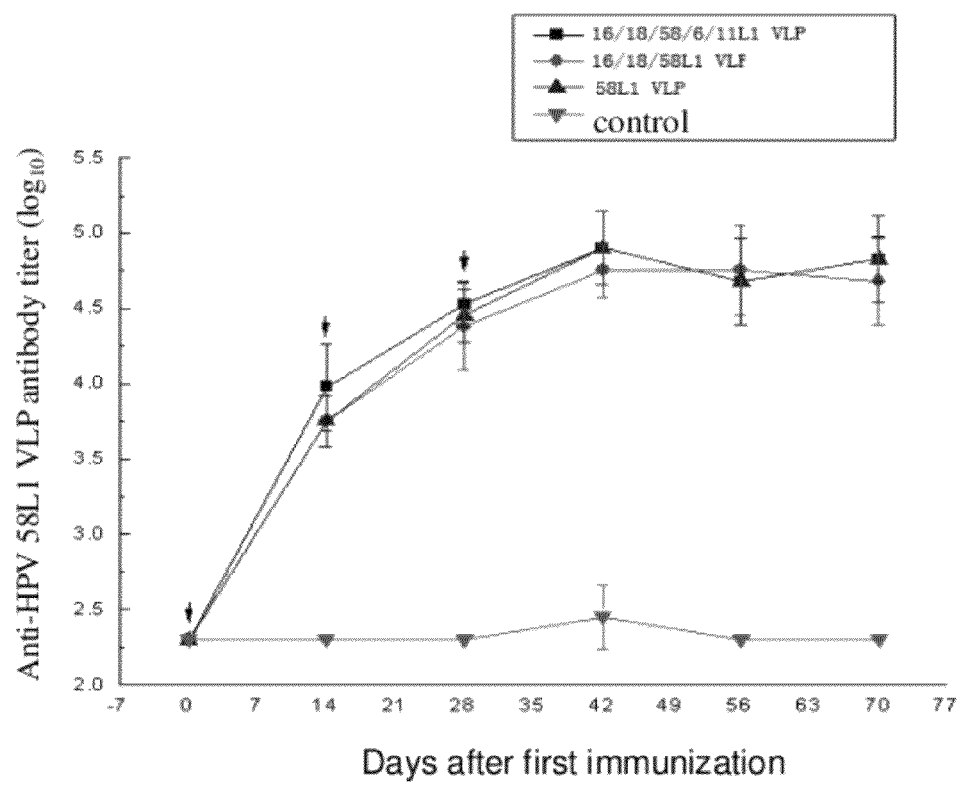
Fig.26. The titers of HPV 58 L1 VLP-specific neutralizing antibodies

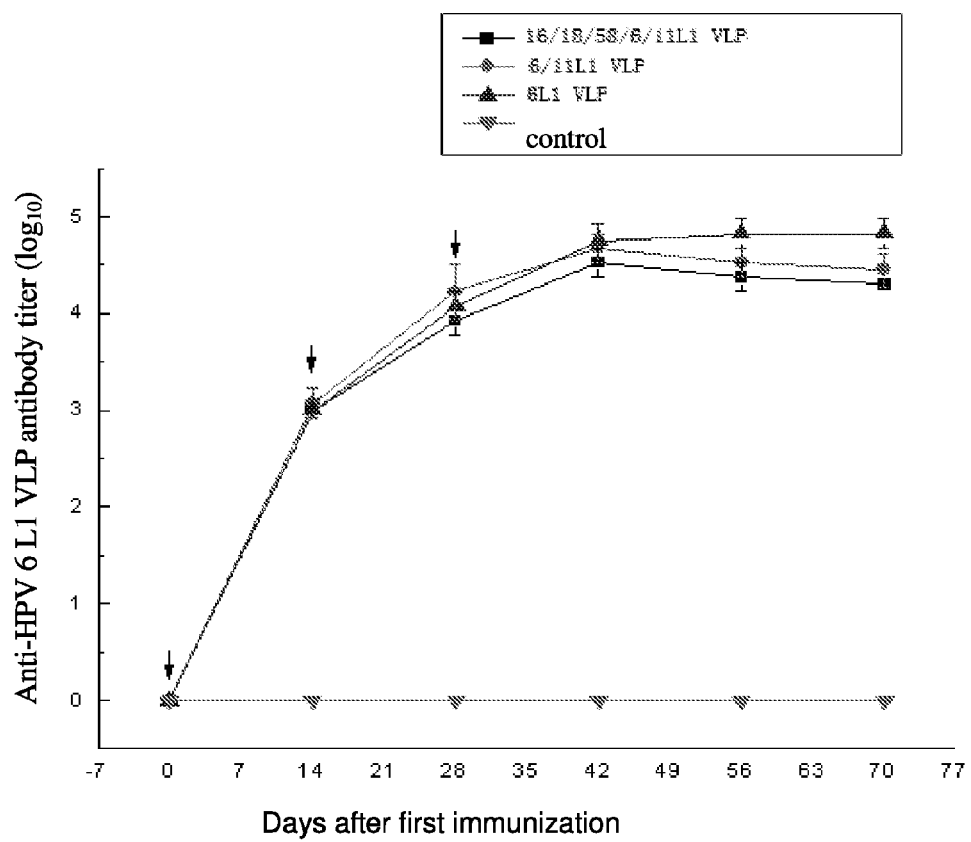
Fig.27. The titers of HPV 6 L1 VLP-specific neutralizing antibodies

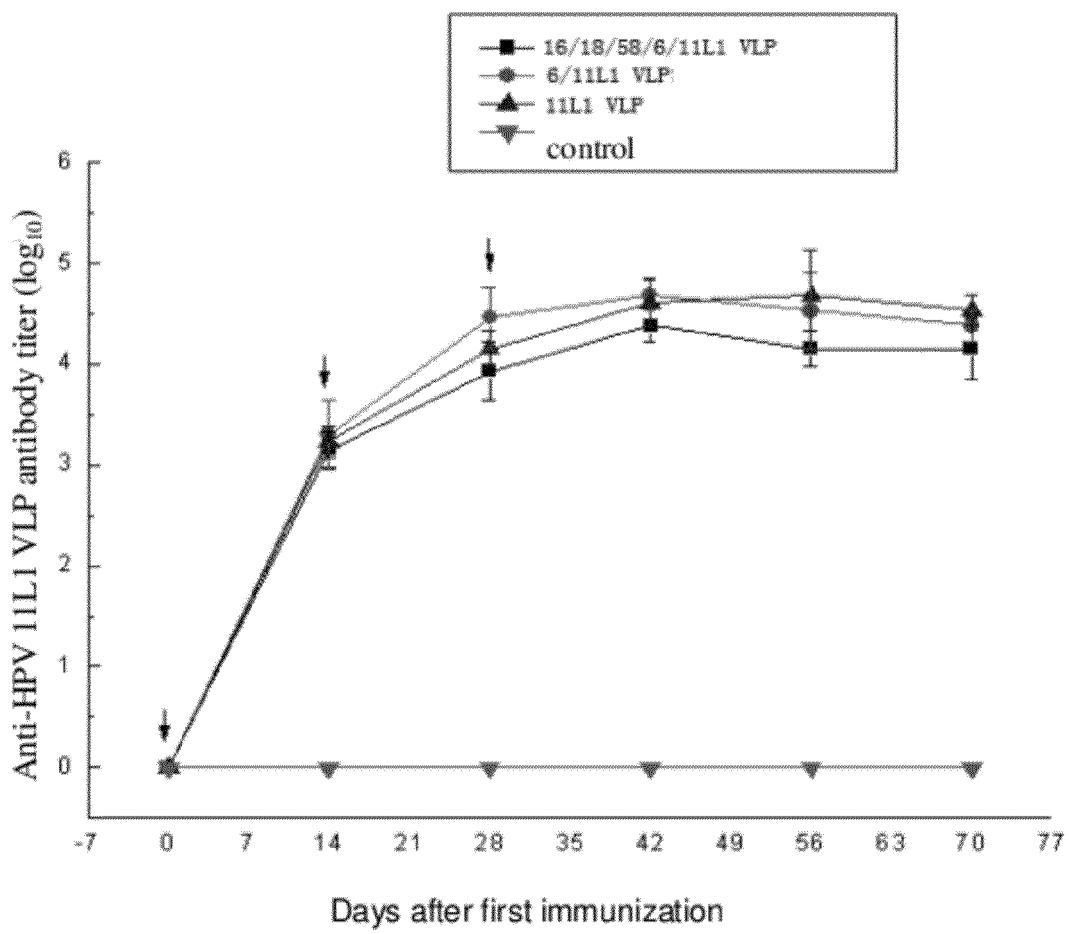
Fig. 28. The titers of HPV 11 L1 VLP-specific neutralizing antibodies

SEQUENCE LISTING

<160> NUMBER OF SEQ ID NOS: 10

<210> SEQ ID NO 1
<211> LENGTH: 1517
<212> TYPE: DNA
<213> ORGANISM: Human papillomavirus type 16

<400> SEQUENCE: 1

```
atgtccctgt ggctgccctc cgaggccacc gtgtacctgc ccccgtgcc cgtgtccaag     60 gtggtgtcca ccgacgagta cgtggctcgc accaacatct actaccacgc tggtacctcc    120
cgcctgctgg cagttggaca tccctatttt cctattaaaa aacctaacaa taacaaaata    180
ttagttccta aagtatcagg attacaatac agggtattta gaatacattt acctgacccc    240
aataagtttg gttttcctga cacctcattt tataatccag atacacagcg gctggtttgg    300
gcctgtgtag gtgttgaggt aggtcgtggt cagccattag gtgtgggcat tagtggccat    360
cctttattaa ataaattgga tgacacagaa aatgctagtg cttatgcagc aaatgcaggt    420
gtggataata gagaatgtat atctatggat tacaaacaaa cacaattgtg tttaattggt    480
tgcaaaccac ctataggga acactggggc aaaggatccc catgtaccaa tgttgcagta    540
aatccaggtg attgtccacc attagagtta ataaacacag ttattcagga tggtgatatg    600
gttgatactg gctttggtgc tatggacttt actacattac aggctaacaa aagtgaagtt    660
ccactggata tttgtacatc tatttgcaaa tatccagatt atattaaaat ggtgtcagaa    720
ccatatggcg acagcttatt tttttatttta cgaagggaac aaatgtttgt tagacattta    780 tttaatagg ctggtgctgt tggtgaaaat gtaccagacg atttatacat taaaggctct    840
gggtctactg caaatttagc cagttcaaat tattttccta cacctagtgg ttctatggtt    900
acctctgatg cccaaatatt caataaacct tattggttac aacgagcaca gggccacaat    960
aatggcattt gttggggtaa ccaactattt gttactgttg ttgatactac acgcagtaca   1020
aatatgtctt tatgtgctgc catatctact tcagaaacta catataaaaa tactaacttt   1080
aaggagtacc tacgacatgg ggaggaatat gatttacagt ttatttttca actgtgcaaa   1140
ataaccttaa ctgcagacgt tatgacatac atacattcta tgaattctac tattttggag   1200
gactggaatt ttggtctaca acctccccca ggaggcacac tagaagatac ttataggttt   1260
gtaacatccc aggcaattgc ttgtcaaaaa catacacctc cagcacctaa agaagatccc   1320
cttaaaaaat acactttttg ggaagtaaat ttaaaggaaa gttttctgc agacctagat   1380 cagtttcctt taggacgcaa attttactaca caagcaggat tgaaggccaa accaaaattt   1440
acattaggaa aacgaaaagc tacacccacc acctcatcta cctctacaac tgctaaacgc   1500
aaaaaacgta gctgtaa                                                 1517
```

<210> SEQ ID NO 2
<211> LENGTH: 1423
<212> TYPE: DNA
<213> ORGANISM: Human papillomavirus type 58

<400> SEQUENCE: 2

```
atgagtgtct ggagaccctc cgaagcaacc gtctatctcc cacccgtccc cgtcagcaaa      60
gtcgtgtcaa ccgacgagta cgtcagcagg acctcaatct actactacgc tggttccagt     120
cgcttgctcg ccgtcggcaa ccctacttc agtattaagt ccccaaacaa caacaagaag      180
gtgctggtcc aaaagtgag cggcctgcaa taccgcgtgt ccgcgtcag gctgcccgac       240
ccaaacaagt tcggcttccc cgacaccagc ttctacaatc ccgacaccca gaggctcgtg     300
tgggcctgcg tgggcttgga gatcggccgc ggccaaccac tcggcgtcgg cgtgtccggc     360
caccctacc tgaacaagtt cgacgatacc gagacatcca atcgctaccc agcccaaccc      420
ggcagcgaca tcgcgagtg tctgagcatg gactacaagc agacccagct gtgcctgatc      480
ggctgcaagc cccaaccgg tgaacactgg gcaagggcg tcgcttgcaa caacaacgcc       540
gccgccaccg actgcccacc cctcgagttg ttcaacagca tcatcgaaga cggcgatatg     600
gtggacaccg gcttcggctg tatggatttc ggcaccctcc aagccaacaa gtccgacgtc     660
cccatcgaca tctgcaattc cacctgtaag taccccgact acctgaagat ggcatccgag     720
ccctacggcg acagcctctt cttcttcctc cgcagggaac aaatgttcgt ccgccatttc     780
ttcaaccgcg ccggcaagtt gggcgaagcc gtgcccgacg atttgtacat caagggcagt     840
ggcaacaccg ccgtcattca gtcctccgca ttcttcccaa ccccctccgg cagcatcgtc     900
acaagcgaga gccagctgtt caacaagccc tactggttgc aaagggccca gggccacaat    960
aacggcatct gttgggcaa ccaactgttc gtcacagtcg tcgacacaac caggtcaacc     1020
aacatgaccc tgtgtaccga ggtgaccaag gagggcacct acaagaacga caacttcaaa    1080
gagtacgtga ggcacgtcga ggagtacgat ctgcaattcg tcttccaatt gtgtaagatc    1140
accttgaccg ccgaaatcat gacctacatc cacaccatgg acagtaacat cctcgaagat    1200
tggcagttcg gcctgacccc cccacccagc gcatccctgc aagataccta ccgcttcgtc    1260
acaagtcaag ccatcacctg tcagaagacc gctccaccca aggagaaaga ggaccccctg    1320
aacaagtaca ccttctggga agtcaatctg aaagagaaat tcagcgccga cttggaccaa    1380
ttcccactcg gcaggaagtt cctgctgcag agcggcttgt aat                      1423
```

<210> SEQ ID NO 3
<211> LENGTH: 1429
<212> TYPE: DNA
<213> ORGANISM: Human papillomavirus type 18

<400> SEQUENCE: 3

```
atggctctct ggagaccctc cgataacaca gtgtacttgc ccccccccag cgtcgcccgc      60
gtcgtgaaca cagacgacta cgtcaccagg acctcaatct tctaccacgc cggttcaagc     120
cgcctgctga ccgtcggcaa ccctacttc cgcgtcccg ccgtggcgg taacaaacaa        180
gacatcccca agtcagcgc ctatcagtac cgcgtgttcc gcgtccaact gcccgatccc     240
aacaagttcg gcctgccga cacctccatc tacaaccccg agacccagag ctggtctgg      300
gcatgcgccg gcgtcgagat cggtaggggc caacccctgg gcgtcggttt gtccggccac    360
cccttctaca caagctgga cgataccgag tcctcccacg cagcaaccag caacgtcagc    420
gaagatgtcc gcgataacgt cagcgtggac tacaaacaaa cccaactgtg catcctcggt    480
```

```
tgcgcacccg ccatcggcga gcattgggcc aagggtaccg cctgcaagag caggcccctg      540
agccaaggtg actgtccacc cctggagttg aagaataccg tcctcgagga cggcgacatg      600
gtggacaccg gctacggcgc aatggatttc tccaccctgc aggacaccaa gtgcgaagtg      660
cccctcgaca tctgccaaag catctgcaag taccccgact acctgcagat gagcgccgac      720
ccctacggcg actccatgtt cttctgtctg agaagggaac aattgttcgc ccgccacttc      780
tggaaccgcg ccggcaccat gggcgatacc gtccccagt ccctgtacat caagggtacc       840
ggcatgaggg ccagcccgg ttcatgcgtc tacagcccaa gccctcggg tagcatcgtc        900 acaagcgatt cccaactctt caacaagccc tactggctgc acaaagccca aggccacaat      960
aacggcgtct gttggcacaa ccagctgttc gtcaccgtcg tggacacaac caggtccaca     1020
aacctgacca tctgcgccag cacccaaagc cccgtgcccg ccagtacga cgccacaaag      1080 ttcaaacaat actcacgcca cgtcgaagag tacgacctcc aattcatctt ccaactctgc     1140
accatcaccc tgaccgccga cgtcatgtcc tacatccact ccatgaactc atccatcctg     1200
gaagactgga atttcggcgt cccaccaccc cccaccacct ccctcgtcga cacctacagg     1260
ttcgtgcaga gcgtcgccat cacatgccag aaagacgccg ccccgccga gaacaaagac      1320 ccatacgaca aactgaaatt ctggaacgtc gacctgaaag agaaattcag cctggatctg     1380
gaccagtacc cattgggcag gaagttcctc gtccaggcgg gtctctaat                 1429

<210> SEQ ID NO 4
<211> LENGTH: 1504
<212> TYPE: DNA
<213> ORGANISM: Human papillomavirus type 6

<400> SEQUENCE: 4
atgtggcgtc cctcagattc aaccgtgtac gtcccccccc ctaatcccgt gtccaaagtc       60
gtcgctaccg acgcctacgt caccaggaca aatatcttct accacgcttc atccagccgc      120
ttgttggccg tcgccacccc ctacttcagc attaagcgcg ctaataagac cgtcgtgccc      180
aaagtcagcg gctaccagta ccgcgtcttc aaagtggtcc tccccgaccc caataaattc      240
gccctgcccg acagctccct cttcgatcct accaccccaaa ggctggtgtg ggcctgtacc     300
ggcctcgaag tgggtcgcgg ccagcccctg ggtgtcggcg tctccggcca cccccttcttg     360 aataagtacg acgacgtgga gaactccggc tccggcggca accccggcca agacaaccgc     420
gtcaacgtgg gcatggacta caagcagaca caattgtgca tggtcggttg cgcccccccc     480
ctgggcgagc actgggcaa aggcaagcag tgcaccaaca cacctgtgca ggctggcgat     540
tgtcctcccc tcgagttgat cacatccgtc atccaagacg gcgatatggt cgacaccggt     600
ttcggcgcca tgaacttcgc cgatctgcag acaaacaaga gcgacgtccc tatcgacatc     660
tgcggcacca cctgtaagta ccccgactac ctccagatgg ccgccgatcc ctacggcgac     720
cgcctcttct tcttcctcag gaaagagcag atgttcgccc gccatttctt caaccgcgct     780
ggcgaggtcg gcgagcccgt ccccgacacc ctcatcatca agggctccgg taatcgcacc     840
agcgtgggct cctccatcta cgtgaacacc cctccggta gcctcgtcag cagcgaagcc       900
cagctgttca acaagcccta ctggttgcag aaagcccaag gccacaataa cggcatctgt     960
tggggcaatc agctcttcgt caccgtcgtg gacacaacca ggtccaccaa catgaccttg     1020
tgcgccagcg tcaccaccag ctccacctac accaacagcg actacaaaga gtacatgagg     1080
cacgtcgaag aatacgacct gcaattcatc ttccagctct gctcaatcac cctgagcgcc     1140
gaggtgatgg cttacatcca taccatgaac cccagcgtcc tcgaagattg gaatttcggt     1200
```

```
ctgagccccc cccccaacgg caccctcgaa gacacctacc gctacgtgca aagccaagct    1260
atcacatgcc aaaagcctac ccccgagaag gagaagccag acccttacaa aaacctgtcc    1320
ttctgggaag tcaatctgaa ggagaaattc agctccgagc tggaccaata ccctttgggc    1380
aggaaattcc tgctccagtc cggctacagg ggccgatcca gcatcaggac cggcgtgaaa    1440
aggcccgccg tcagcaaagc tagcgccgct cctaagagga gagggctaa gacaaagcgt     1500 taat                                                                 1504
```

<210> SEQ ID NO 5
<211> LENGTH: 1507
<212> TYPE: DNA
<213> ORGANISM: Human papillomavirus type 11

<400> SEQUENCE: 5

```
atgtggcgtc cctcagattc aaccgtgtac gtccccccccc ctaatcccgt gtccaaagtc    60
gtcgctaccg acgcctacgt caagaggaca aatatcttct accacgcttc atccagccgc    120
ttgttggccg tcggccaccc ctactacagc attaagaagg tcaataagac cgtcgtgccc    180
aaagtcagcg gctaccagta ccgcgtcttc aaagtggtcc tccccgaccc caataaattc    240
gccctgcccg acagctccct cttcgatcct accacccaaa ggctggtgtg ggcctgtacc    300
ggcctcgaag tgggtcgcgg ccagcccctg ggtgtcggcg tctccggcca cccctcttg     360 aataagtacg acgacgtgga gaactccggc ggctacggcg caaccccgg ccaagacaac     420 cgcgtcaacg tgggcatgga ctacaagcag acacaattgt gcatggtcgg ttgcgccccc   480
cccctgggcg agcactgggg caaaggcacc cagtgcagca cacaagcgt gcagaacggc    540 gattgtcctc ccctcgagtt gatcacatcc gtcatccaag acggcgatat ggtcgacacc    600
ggtttcggcg ccatgaactt cgccgatctg cagacaaaca gagcgacgt cccctttggac   660 atctgcggca ccgtgtgtaa gtaccccgac tacctccaga tggccgccga tccctacgc    720 gaccgcctct tcttctacct caggaaagag cagatgttcg cccgccatt cttcaaccgc    780 gctggcaccg tcggcgagcc cgtccccgac gatctcctcg tgaagggcgg caacaatcgc   840
agcagcgtgg cctcctccat ctacgtgcac accccctccg gtagcctcgt cagcagcgaa   900
gcccagctgt tcaacaagcc ctactggttg cagaaagccc aaggccacaa taacggcatc    960
tgttggggca atcatctctt cgtcaccgtc gtggacacaa ccaggtccac caacatgacc   1020
ttgtgcgcca gcgtcagcaa gagcgccacc tacaccaaca gcgactacaa agagtacatg   1080
aggcacgtca agaattcga cctgcaattc atcttccagc tctgctcaat caccctgagc   1140
gccgaggtga tggcttacat ccataccatg aaccccagcg tcctcgaaga ttggaatttc   1200
ggtctgagcc cccccccaa cggcaccctc gaagacacct accgctacgt gcaaagccaa    1260
gctatcacat gccaaaagcc taccccgag aaggagaagc aagacccta caaagacatg    1320 tccttctggg aagtcaatct gaaggagaaa ttcagctccg agctggacca attccctttg   1380
ggcaggaaat tcctgctcca gtccggctac aggggccgaa ccagcgccag accggcatc    1440 aaaaggcccg ccgtcagcaa acctagcacc gctcctaaga ggaagaggac aaagacaaag   1500
aaataat                                                             1507
```

<210> SEQ ID NO 6
<211> LENGTH: 1518
<212> TYPE: DNA
<213> ORGANISM: Human papillomavirus type 16

<400> SEQUENCE: 6

-continued

```
atgtctcttt ggctgcctag tgaggccact gtctacttgc ctcctgtccc agtatctaag      60
gttgtaagca cggatgaata tgttgcacgc acaaacatat attatcatgc aggaacatcc     120
agactacttg cagttggaca tccctatttt cctattaaaa aacctaacaa taacaaaata     180
ttagttccta aagtatcagg attacaatac agggtattta gaatacattt acctgacccc     240
aataagtttg gttttcctga cacctcattt tataatccag atacacagcg gctggtttgg     300
gcctgtgtag gtgttgaggt aggtcgtggt cagccattag gtgtgggcat tagtggccat     360
cctttattaa ataaattgga tgacacagaa aatgctagtg cttatgcagc aaatgcaggt     420
gtggataata gagaatgtat atctatggat tacaaacaaa cacaattgtg tttaattggt     480
tgcaaaccac ctataggga acactggggc aaaggatccc catgtaccaa tgttgcagta      540
aatccaggtg attgtccacc attagagtta ataaacacag ttattcagga tggtgatatg     600
gttgacactg gctttggtgc tatggacttt actacattac aggctaacaa aagtgaagtt     660
ccactggata tttgtacatc tatttgcaaa tatccagatt atattaaaat ggtgtcagaa     720
ccatatggcg acagcttatt ttttatttta cgaagggaac aaatgtttgt tagacattta     780
tttaataggg ctggtgctgt tggtgaaaat gtaccagacg atttatacat taaaggctct     840
gggtctactg caaatttagc cagttcaaat tattttccta cacctagtgg ttctatggtt     900
acctctgatg cccaaatatt caataaacct tattggttac aacgagcaca gggccacaat     960
aatggcattt gttggggtaa ccaactattt gttactgttg ttgatactac acgcagtaca    1020
aatatgtcat tatgtgctgc catatctact tcagaaacta catataaaaa tactaacttt    1080
aaggagtacc tacgacatgg ggaggaatat gatttacagt ttatttttca actgtgcaaa    1140
ataaccttaa ctgcagacgt tatgacatac atacattcta tgaattccac tattttggag    1200
gactggaatt ttggtctaca acctccccca ggaggcacac tagaagatac ttataggttt    1260
gtaacatccc aggcaattgc ttgtcaaaaa catacacctc cagcacctaa agaagatccc    1320
cttaaaaaat acacttttg ggaagtaaat ttaaaggaaa agttttctgc agacctagat    1380
cagtttcctt taggacgcaa attttttacta caagcaggat tgaaggccaa accaaaattt    1440
acattaggaa aacgaaaagc tacacccacc acctcatcta cctctacaac tgctaaacgc    1500
aaaaaacgta agctgtaa                                                 1518
```

<210> SEQ ID NO 7
<211> LENGTH: 1497
<212> TYPE: DNA
<213> ORGANISM: Human papillomavirus type 58

<400> SEQUENCE: 7

```
atgtccgtgt ggcggcctag tgaggccact gtgtacctgc ctcctgtgcc tgtgtctaag      60
gttgtaagca ctgatgaata tgtgtcacgc acaagcattt attattatgc tggcagttcc     120
agactttggg ctgttggcaa tccatatttt cccatcaaaa gtcccaataa caataaaaaa     180
gtattagttc ccaaggtatc aggcttacag tatagggtct ttagggtgcg tttacctgat     240
cccaataaat ttgttttcc tgatacatct tttataacc ctgatacaca acgtttggtc      300
tgggcatgtg taggccttga aataggtagg ggacagccat ggggtgttgg cgtaagtggt     360
catccttatt aaataaaatt tgatgacact gaaaccagta acagatatcc cgcacagcca     420
gggtctgata cagggaatg cttatctatg gattataaac aaacacaatt atgtttaatt     480
ggctgtaaac ctcccactgg tgagcattgg ggtaaaggtg ttgcctgtaa caataatgca     540
gctgctactg attgtcctcc attggaactt tttaattcta ttattgagga tggtgacatg     600
```

```
gtagatacag ggtttggatg catggacttt ggtacattgc aggctaataa aagtgatgtg    660
cctattgata tttgtaacag tacatgcaaa tatccagatt attaaaaaat ggccagtgaa    720
ccttatgggg atagtttgtt cttttttctt agacgtgagc agatgtttgt tagacacttt    780
tttaataggg ctggaaaact tggcgaggct gtcccggatg acctttatat taaagggtcc    840
ggtaatactg cagttatcca aagtagtgca ttttttccaa ctcctagtgg ctctatagtt    900
acctcagaat cacaattatt taataagcct tattggctac agcgtgcaca aggtcataac    960
aatggcattt gctggggcaa tcagttattt gttaccgtgg ttgataccac tcgtagcact   1020
aatatgacat tatgcactga agtaactaag gaaggtacat ataaaaatga aattttaag    1080 gaatatgtac gtcatgttga agaatatgac ttacagtttg tttttcagct ttgcaaaatt   1140
acactaactg cagagataat gacatatata catactatgg attccaatat tttggaggac   1200
tggcaatttg gtttaacacc tcctccgtct gccagtttac aggacacata tagatttgtt   1260
acctcccagg ctattacttg ccaaaaaaca gcacccccta agaaaagga agatccatta    1320 aataaatata cttttttggga ggttaactta aaggaaaagt tttctgcaga tctagatcag   1380
tttcctttgg gacgaaagtt tttattacaa tcaggcctta agcaaagcc cagactaaaa   1440 cgttcggccc ctactacccg tgcaccatcc accaaacgca aaaggttaa aaaataa     1497

<210> SEQ ID NO 8
<211> LENGTH: 1524
<212> TYPE: DNA
<213> ORGANISM: Human papillomavirus type 18

<400> SEQUENCE: 8
atggctttgt ggcggcctag tgacaatacc gtatatcttc cacctccttc tgtggcaaga     60
gttgtaaata ccgatgatta tgtgactccc acaagcatat tttatcatgc tggcagctct    120
agattattaa ctgttggtaa tccatatttt agggttcctg caggtggtgg caataagcag    180
gatattccta aggtttctgc ataccaatat agagtattta gggtgcagtt acctgaccca    240
aataaatttg gttacctga tactagtatt tataatcctg aaacacaacg tttagtgtgg    300
gcctgtgctg gagtggaaat tggccgtggt cagcctttag tgttggcct tagtgggcat    360 ccatttttata ataaattaga tgacactgaa agttcccatg ccgccacgtc taatgtttct    420
gaggacgtta gggacaatgt gtctgtagat tataagcaga cacagttatg tattttgggc    480
tgtgcccctg ctattgggga acactgggct aaaggcactg cttgtaaatc gcgtcctta    540 tcacagggcg attgcccccc tttagaactt aaaaacacag ttttggaaga tggtgatatg    600
gtagatactg gatatggtgc catggacttt agtacattgc aagatactaa atgtgaggta    660
ccattggata tttgtcagtc tatttgtaaa tatcctgatt atttacaaat gtctgcagat    720
cctatggggg attccatgtt ttttgctta cggcgtgagc agctttttgc taggcatttt    780
tggaatagag caggtactat gggtgacact gtgcctcaat ccttatatat taaaggcaca    840
ggtatgcctg cttcacctgg cagctgtgtg tattctccct ctccaagtgg ctctattgtt    900
acctctgact cccagttgtt taataaacca tattggttac ataaggcaca gggtcataac    960
aatggtgttt gctggcataa tcaattattt gttactgtgg tagataccac tcccagtacc   1020
aatttaacaa tatgtgcttc tacacagtct cctgtacctg gcaatatga tgctaccaaa    1080 tttaagcagt atagcagaca tgttgaggaa tatgatttgc agtttatttt tcagttgtgt    1140
actattactt taactgcaga tgttatgtcc tatattcata gtatgaatag cagtatttta    1200
gaggattgga actttggtgt tcccccccc ccaactacta gttggtgga tacatatcgt    1260
```

| | |
|---|---:|
| tttgtacaat ctgttgctat tacctgtcaa aaggatgctg caccggctga aaataaggat | 1320 |
| ccctatgata agttaaagtt ttggaatgtg gatttaaagg aaaagttttc tttagactta | 1380 |
| gatcaatatc cccttggacg taaattttg gttcaggctg gattgcgtcg caagcccacc | 1440 |
| ataggccctc gcaaacgttc tgctccatct gccactacgt cttctaaacc tgccaagcgt | 1500 |
| gtgcgtgtac gtgccaggaa gtaa | 1524 |

<210> SEQ ID NO 9
<211> LENGTH: 1503
<212> TYPE: DNA
<213> ORGANISM: Human papillomavirus type 6

<400> SEQUENCE: 9

| | |
|---|---:|
| atgtggcggc ctagcgacag cacagtatat gtgcctcctc ctaaccctgt atccaaagtt | 60 |
| gttgccacgg atgcttatgt tactcgcacc aacatatttt atcatgccag cagttctaga | 120 |
| cttcttgcag tgggacatcc ttatttttcc ataaaacggg ctaacaaaac tgttgtgcca | 180 |
| aaggtgtcag gatatcaata cagggtattt aaggtggtgt taccagatcc taacaaattt | 240 |
| gcattgcctg actcgtctct tttcgatccc acaacacaac gttagtatg ggcatgcaca | 300 |
| ggcctagagg tgggcagggg acagccatta ggtgtgggtg taagtggaca tccttttcta | 360 |
| aataaatatg atgatgttga aaattcaggg agtggtggta accctggaca ggataacagg | 420 |
| gttaatgtag gtatggatta taaacaaaca caattatgca tggttggatg tgccccccct | 480 |
| ttgggcgagc attggggtaa aggtaaacag tgtactaata cacctgtaca ggctggtgac | 540 |
| tgcccgccct tagaacttat taccagtgtt atacaggatg gcgatatggt tgacacaggc | 600 |
| tttggtgcta tgaattttgc tgatttgcag accaataaat cagatgttcc tattgacata | 660 |
| tgtggcacta catgtaaata tccagattat ttacaaatgg ctgcagaccc atatggtgat | 720 |
| agattatttt ttttctctacg gaaggaacaa atgtttgcca gacatttttt taacagggct | 780 |
| ggcgaggtgg gggaacctgt gcctgatact cttataatta agggtagtgg aaatcgcacg | 840 |
| tctgtaggga gtagtatata tgttaacacc ccgagcggct cttttggtgtc ctctgaggca | 900 |
| caattgttta ataagccata ttggctacaa aaagcccagg gacataacaa tggtatttgt | 960 |
| tggggtaatc aactgtttgt tactgtggta gataccacac gcagtaccaa catgacatta | 1020 |
| tgtgcatccg taactacatc ttccacatac accaattctg attataaaga gtacatgcgt | 1080 |
| catgtggaag agtatgattt acaatttatt tttcaattat gtagcattac attgtctgct | 1140 |
| gaagtaatgg cctatattca cacaatgaat ccctctgttt tggaagactg gaactttggg | 1200 |
| ttatcgccct ccccaaatgg tacattagaa gatacctata ggtatgtgca gtcacaggcc | 1260 |
| attacctgtc aaaagcccac tcctgaaaag gagaagccag atccctataa aaaccttagt | 1320 |
| ttttgggagg ttaatttaaa agaaaagttt tctagtgaat tggatcagta tcctttggga | 1380 |
| cgcaagtttt tgttacaaag tggatatagg ggacggtcct ctattcgtac aggtgttaag | 1440 |
| cgccctgctg tttccaaagc ctctgctgcc cctaaacgta agcgcgccaa aactaaaagg | 1500 |
| taa | 1503 |

<210> SEQ ID NO 10
<211> LENGTH: 1506
<212> TYPE: DNA
<213> ORGANISM: Human papillomavirus type 11

<400> SEQUENCE: 10

| | |
|---|---:|
| atgtggcggc ctagcgacag cacagtatat gtgcctcctc ccaaccctgt atccaaggtt | 60 |

-continued

```
gttgccacgg atgcgtatgt taaacgcacc aacatatttt atcacgccag cagttctaga    120
ctccttgctg tgggacatcc atattactct atcaaaaaag ttaacaaaac agttgtacca    180
aaggtgtctg gatatcaata tagagtgttt aaggtagtgt tgccagatcc taacaagttt    240
gcattacctg attcatctct gtttgacccc actacacagc gtttagtatg ggcgtgcaca    300
gggttggagg taggcagggg tcaaccttta ggcgttggtg ttagtgggca tccattgcta    360
aacaaatatg atgatgtaga aaatagtggt gggtatggtg gtaatcctgg tcaggataat    420
agggttaatg taggtatgga ttataaacaa acccagctat gtatggtggg ctgtgctcca    480
ccgttaggtg aacattgggg taagggtaca caatgttcaa atacctctgt acaaaatggt    540
gactgccccc cgttggaact tattaccagt gttatacagg atggggacat ggttgataca    600
ggctttggtg ctatgaattt tgcagactta caaaccaata aatcggatgt tccccttgat    660
atttgtggaa ctgtctgcaa atatcctgat tatttgcaaa tggctgcaga cccttatggt    720
gataggttgt ttttttattt gcgaaaggaa caaatgtttg ctagacactt ttttaatagg    780
gccggtactg tgggggaacc tgtgcctgat gacctgttgg taaaaggggg taataataga    840
tcatctgtag ctagtagtat ttatgtacat acacctagtg gctcattggt gtcttcagag    900
gctcaattat ttaataaacc atattggctt caaaaggctc agggacataa caatggtatt    960
tgctggggaa accacttgtt tgttactgtg gtagatacca cacgcagtac aaatatgaca   1020
ctatgtgcat ctgtgtctaa atctgctaca tacactaatt cagattataa ggaatacatg   1080
cgccatgtga aagagtttga tttacagttt atttttcaat tgtgtagcat tacattatct   1140
gcagaagtca tggcctatat acacacaatg aatccttctg ttttggagga ctggaacttt   1200
ggtttatcgc ctccaccaaa tggtacactg gaggatactt atagatatgt acagtcacag   1260
gccattacct gtcagaaacc cacacctgaa aaagaaaaac aggatcccta taaggatatg   1320
agtttttggg aggttaactt aaaagaaaag ttttcaagtg aattagatca gtttcccctt   1380
ggacgtaagt tttattgcaa aagtggatat cgaggacgga cgtctgctcg tacaggtata   1440
aagcgcccag ctgtgtctaa gccctctaca gcccccaaac gaaaacgtac caaaaccaaa   1500
aagtaa                                                              1506
```

VIRUS-LIKE PARTICLES OF CAPSID PROTEINS FROM HUMAN PAPILLOMAVIRUS TYPE 16/58/18/6/11 AND THE METHOD FOR PREPARATION AND THE USES THEREOF

RELATED APPLICATIONS

This patent application is a National Stage of International Application Serial No. PCT/CN2007/070715 filed on Sep. 18, 2007, which claims the benefit of Chinese Application Serial No. CN200610127387.2 filed on Sep. 18, 2006, the disclosures of which are all incorporated herein by reference in their entireties.

FIELD OF THE INVENTION

The present invention relates to human papillomavirus virus-like particles (HPV VLPs), and in particular, expressing optimally modified HPV 16 L1, HPV 58 L1, HPV 18 L1, HPV 6 L1 and HPV 11 L1 genes in insect cells to produce proteins encoded by the above said five genes, and to obtain VLPs of HPV 16, 58, 18, 6 and 11 L1s. The present invention also relates to the multivalent vaccines comprising those five genotypes of HPV VLPs, and methods for preparation and the uses thereof.

BACKGROUND OF THE INVENTION

Human papillomavirus (HPV) is a class of small non-enveloped DNA virus; currently more than 100 genotypes of HPVs have been identified. HPV primarily infects human host through squamous and mucosal epithelia to cause benign and malignant epithelial neoplasia. Based on tissue-tropism of HPVs, they can be classified into cutaneous type and mucosal type. The mucosal type of HPVs can be further divided into two subtypes according to their relationships with benign and malignant epithelial neoplasia: the low-risk type, which is associated with development of precondyloma acuminate and other benign lesions, and the high-risk type, which can give rise to precancerous lesions of cervical cancer and other cancers. Studies have shown that persistent infection of the high-risk type HPV is causally linked to cervical cancer and HPV positives can be detected in about over 99.7% cervical cancer patients. [Walboomers, J. M. et al. J. Pathol. 1999, 189:12-19]. In addition, above 90% of anus and vaginal squamous carcinoma, 40% of vulva and penile cancer, 12% of oropharyngeal cancer and 3% of oral cancer are associated with infections of the high-risk type HPVs [Lacey C J N. Medicine, 2005, 33(10):51-55]. The International Agency for Research on Cancer (IARC) analyzed 3607 cervical cancer samples obtained from 25 countries of the world (excluding East Asia) and 15 high-risk types of HPV were found. Based on the positive infection rate, among the highest were HPV 16(53.5%), 18(17.2%), 45(6.7%), 31(2.9%), 33(2.6%), 52(2.3%), and 58(2.2%), respectively [Munoz, N. et al. Int. J. Cancer, 2004, 111: 78-285]. Research from our team and others in China showed that HPV 16 was the most frequently detected type among Chinese patients with pre-cancerous lesions and cervical cancer, while HPV 58 and HPV 18 were next to HPV 16. For example, Chen et al. found that in Sichuan province, the infection frequencies of HPV 16, 58 and 18 in patients with cervical cancer were 78.6%, 20.0% and 9.7%, respectively; studies by Liu et al. with 815 cervical cancer samples from fourteen provinces in China also demonstrated that HPV 16 positive was most frequently detected and HPV 58 positive ranked the second; in addition, the positive frequencies of HPV 58 in cervical cancer patients was 12.3-17.5% in Northeastern China, Southeastern China and Shanxi province, 12.3-19.9% in Taiwan and 31.5-33.3% in Hong Kong [Si J Y, Lee K, Han R C, et al. J Cancer Res Clin Oncology. 1991, 117: 454-459; Liu B Y, Li J, De Villiers E M et al. Chinese Journal of Experimental and Clinical Virology, 1996, 10:118-121; Hao L, Ma Y Y, Mo J S, et al. Gynecologic Oncology, 2006, 101(1):40-45; Chan P K, Li W H, Chan MY, et al. J Med Virol. 1999, 59 (2):232-238; Chen C A, Liu C Y, Chou H H, Chou C Y, et al. Int J Gynecol Cancer. 2006, 16(5):1801-8]. The above studies demonstrated that besides HPV 16, HPV 58 is another important etiologic cause for cervical cancer among Chinese women, i.e. HPV 16, 58 and 18 are among the viral genotypes that are closely associated with the development of cervical cancer in China. Infection of HPV 58 is very common in Japan, Korea and other East Asian countries. Currently, 12 low-risk type HPVs (6, 11, 40, 42, 43, 44, 54, 61, 70, 72, 81 and CP6108) have been identified; infections of these HPVs generally cause genital warts. Condyloma acuminate is a common type of genital warts and is the second highest-occurring sexually transmitted disease in China (next to gonorrhea). It is mainly transmitted via sexual routes. Over the past decade, the morbidity of condyloma acuminate increased constantly. Research has demonstrated that in tissues of Chinese patients with condyloma acuminate, 82% were HPV 6 positive and 6% were HPV 11 positive.

Currently there is limitation in clinical therapeutics for condyloma acuminate and later stage cervical cancer. There is no effective vaccine in the Chinese domestic market. Pap smear screen for cervical cancer is relatively expensive and is only suitable for economically advanced area. Although effective methods for detecting HPV infections are available and the majority cervical cancer patients can be treated, among the detected HPV positives, about 35% patients would still eventually develop persistent infections or tumors. In rural developing area where cervical cancer possesses high incidence rates, pap smear screen cannot be widely applied due to economic and cultural reasons. Therefore, develop effective prophylactic vaccination provides a better solution over pap smear screen in preventing cervical cancer.

L1 protein may be self-assembled into virus-like particles (VLPs) when expressed in vitro. Similar to naturally-occurring viruses, VLPs may induce protective neutralizing antibodies. However, such antibodies are highly genotype-specific and usually have no cross-neutralizing activities. Thus, vaccination with one HPV VLP genotype is not able to prevent the infection of other HPV genotypes. Clinical studies showed that both vaccines have high safety and immune protection effects [Harper D M, et al. Lancet. 2004, 364: 1757-1765; Harper D M et al. The Lancet. 2006; Internet: 1-9]. However, since none of the two vaccines contains HPV58, they do not meet the requirements for preventing HPV-infection associated diseases in China and other East Asian countries. Chinese patent application CN 1869215A has released modified HPV16, 58 and 6 L1 genes. In addition, given that HPV-infection and infection-associated diseases have high incidence rates in developing countries, the key point of successfully developing HPV vaccines would be producing high expression level of the L1 protein in vitro, thus reduce the cost of vaccine manufacturing.

However, wild type HPV L1 (L1wt) genes amplified from patients possess several characters including preferred codon usage bias, hypothetical transcription stop codons (e.g. AT rich structures such as TATATA, TAGATA, and TACATA), long GC rich stems of mRNAs and their complex secondary structures. Examples including the existence of RNA transcription inhibiting element that located at the N-terminus of wild type HPV 16 L1. These gene characters result in low expression level of the L1 protein in vitro, prohibit large-scale VLP production and further prohibit the manufacturing of low-cost vaccines. To solve the limitation of the current technology, the present invention provides optimized HPV 16, 58, 18, 6 and 11 L1 genes that may produce high level gene and protein expressions of L1 in insect cells, and obtain HPV 16, 58, 18, 6 and 11 VLPs. The present invention also provides multivalent vaccines comprising the above said five genotypes of HPV VLPs suitable for prevention and treatment of HPV-infection associated diseases in China and other East Asian countries.

SUMMARY OF THE INVENTION

In the first aspect the present invention provides optimally modified HPV L1 (L1M) gene sequences, comprising nucleotide sequence of HPV 16 L1M gene as set forth in SEQ ID NO:1; the nucleotide sequence of HPV 58 L1M gene as set forth in SEQ ID NO:2; the nucleotide sequence of HPV 18 L1M gene as set forth in SEQ ID NO:3; the nucleotide sequence of HPV 6 L1M gene as set forth in SEQ ID NO:4; and the nucleotide sequence of HPV 11 L1M gene as set forth in SEQ ID NO:5.

Preferably, the optimally modified HPV 58 L1M gene used herein contains a 25-amino acid truncation from the C-terminus (of the HPV 58 L1 protein coding sequence); preferably, the optimally modified HPV 18 L1M gene used herein contains a 32-amino acid truncation from the C-terminus (of the HPV 18 L1 protein coding sequence).

In another aspect, the present invention provides recombinant pFastBacI plasmids containing said optimally modified HPV L1 gene sequences; recombinant Bacmids generated from said recombinant pFastBacI plasmids; recombinant *E. coli* DH 10Bac strains carrying said recombinant Bacmids; recombinant baculoviruses containing said recombinant Bacmids; and the Sf9 insect cells infected by said recombinant baculoviruses.

In the third aspect, the present invention provides a method of optimally modifying the HPV16, 58, 18, 6 and 11 major capsid protein L1 genes, comprising steps or step combinations of: (1) using codons with the insect cell preferred codon usage bias; (2) removing hypothetical splicing donor and receiver regions, removing hypothetical stop signals, removing hnRNP-H binding sites; (3) removing long stems formed by GC pairs in RNA secondary structure; (4) reducing the length of C/T-rich tracts; (5) simplifying the complexity of the starting area of the secondary structure of mRNA to make it located at an easily accessed loop area.

In the fourth aspect, the present invention provides an anti-HPV infection vaccine comprising the virus-like particles (VLP) assembled by proteins encoded by the optimally modified gene sequences described in any one of Claim 1 to 5.

Preferred anti-HPV infection vaccine may also contain L2 proteins or derivatives thereof.

In the fifth aspect, the present invention further provides an anti-HPV infection vaccines composition containing two or more VLPs selected from HPV 16 L1 VLP, HPV 58 L1 VLP, HPV 18 L1 VLP, HPV 6 L1 VLP and HPV 11 L1 VLP.

Preferred vaccine compositions also include L1 proteins from VLPs of additional HPV genotypes or functional derivatives thereof.

HPV 16, 58, 18, 6 and 11 L1 VLPs produced by the baculovirus-insect cell expression system in the present invention have size and structural characteristics similar to those of the naturally-occurring viruses. In addition, such VLPs possess same biological characters as the naturally-occurring viruses to hemagglutinate mouse erythrocytes and the ability to induce specific humoral and cellular immune responses. Compare with VLP vaccines produced from corresponding wild type HPV L1 genes, using the above said five types of modified HPV L1 genes provides significantly increased yield of the VLP protein; administration of a mixture of all five VLPs, or mixtures of various VLP combinations, such as a HPV16, 58, 18 VLPs combination and a HPV 6, 11 VLPs combination, may elicit synchronized species-specific immune responses to prevent HPV infections of corresponding genotypes and infection associated diseases.

DESCRIPTION OF THE FIGURES

SEQ ID NO: 1. DNA sequence of optimally modified HPV 16 L1 gene.

SEQ ID NO: 2. DNA sequence of optimally modified HPV 58 L1 gene.

SEQ ID NO: 3. DNA sequence of optimally modified HPV 18 L1 gene.

SEQ ID NO: 4. DNA sequence of optimally modified HPV 6 L1 gene.

SEQ ID NO: 5. DNA sequence of optimally modified HPV 11 L1 gene.

FIG. 1 is a sequence alignment of optimally modified HPV 16 (SEQ ID NO:1) and corresponding wild type L1 genes (SEQ ID NO:6).

FIG. 2 is a sequence alignment of optimally modified HPV 58 (SEQ ID NO:2) and corresponding wild type L1 genes (SEQ ID NO:7).

FIG. 3 is a sequence alignment of optimally modified HPV 18 (SEQ ID NO:3) and corresponding wild type L1 genes (SEQ ID NO:8).

FIG. 4 is a sequence alignment of optimally modified HPV 6 (SEQ ID NO:4) and corresponding wild type L1 genes (SEQ ID NO:9).

FIG. 5 is a sequence alignment of optimally modified HPV 11 (SEQ ID NO:5) and corresponding wild type L1 genes (SEQ ID NO:10).

FIG. 6 is a graph depicting the plasmid map of pFastBacI-HPV 16 L1M, showing that the optimally modified HPV 16 L1 gene is inserted in the recombinant plasmid.

FIG. 7 is a graph depicting the plasmid map of pFastBacI-HPV 58 L1M, showing that the optimally modified HPV 58 L1 gene is inserted in the recombinant plasmid.

FIG. 8 is a graph depicting the plasmid map of pFastBacI-HPV 18 L1M, showing that the optimally modified HPV 18 L1 gene is inserted in the recombinant plasmid.

FIG. 9 is a graph depicting the plasmid map of pFastBacI-HPV 6 L1M, showing that the optimally modified HPV 6 L1 gene is inserted in the recombinant plasmid.

FIG. 10 is a graph depicting the plasmid map of pFastBacI-HPV 11 L1M, showing that the optimally modified HPV 11 L1 gene is inserted in the recombinant plasmid.

FIG. 11 shows the analysis result of gene expression of the optimally modified HPV 11 L1. Panel A is a representation of the L1 protein expression level in infected cells analyzed by SDS-PAGE gel/Coomassie Blue. Lane 1 represents Sf9 cell lysate, lane 2 represents Sf9 cell lysate infected with HPV 11 L1wt recombinant baculovirus, lane 3 represents Sf9 cell lysate infected with HPV 11 L1M recombinant baculovirus. Panel B is representation of the HPV 11 L1 protein level anglicized by Western blot. Lane 1 represents the L1 protein level expressed by the HPV 11 L1M gene, lane 2 represents the L1 protein level expressed by the HPV 11 L1wt gene. The lower panel table is an illustration of the Optical Density (OD) values of the bands showing in panel B.

FIG. 12 is a representation of the modified HPV 6 L1 protein expression level analyzing by Western blot. Lane 1 represents the protein expression level of the HPV 6 L1M gene, lane 2 represents the protein expression level of the HPV 6 L1wt gene. The lower panel table is an illustration of the Optical Density (OD) values of the bands showing in the upper panel.

FIG. 13 is a representation of the modified HPV 16 L1 protein expression level analyzing by Western blot. Lane 1 represents the protein expression level of the HPV 16 L1M gene; lane 2 represents the protein expression level of the HPV 16 L1wt gene. The lower panel table is an illustration of the Optical Density (OD) values of the bands showing in the upper panel.

FIG. 14 is a representation of the modified HPV 58 L1 protein expression level analyzing by Western blot. Lane 1 represents the protein expression level of the HPV 58 L1M gene, lane 2 represents the protein expression level of the HPV 58 L1wt gene. The lower panel table is an illustration of the Optical Density (OD) values of the bands showing in the upper panel.

FIG. 15 is a representation of the modified HPV 18 L1 protein expression level analyzing by Western blot. Lane 1 represents the protein expression level of the HPV 18 L1M gene, lane 2 represents the protein expression level of the HPV 18 L1wt gene. The lower panel table is an illustration of the Optical Density (OD) values of the bands showing in the upper panel.

FIG. 16 is a figure showing the transmission electron microscopy picture of purified HPV 16 L1 VLP. Bar=50 nm FIG. 17 is a figure showing the transmission electron microscopy picture of purified HPV 58 L1 VLP. Bar=50 nm FIG. 18 is a figure showing the transmission electron microscopy picture of purified HPV 18 L1 VLP. Bar=50 nm FIG. 19 is a figure showing the transmission electron microscopy picture of purified HPV 6 L1 VLP. Bar=50 nm FIG. 20 is a figure showing the transmission electron microscopy picture of purified HPV 11 L1 VLP. Bar=50 nm FIG. 21 is a figure showing the result of the hemagglutination assay of HPV 16 L1 VLP FIG. 22 is a graph depicting the conformation-dependent characterization of serum neutralizing antibodies induced by said five genotypes of HPV L1 VLPs in immunized mice FIG. 23 is a graph depicting the splenocytes proliferation assay of said five genotypes of HPV L1 VLPs in immunized mice FIG. 24 is a graph depicting the titers of HPV 16 L1 VLP-specific serum antibodies in immunized mice induced by administration of the mixture of said five genotypes of HPV L1 VLPs (16, 18, 58, 6 and 11), the mixture of three genotypes of HPV L1 VLPs (16, 18 and 58) and HPV 16 L1 VLP. Arrows indicate three immunization time points.

FIG. 25 is a graph depicting the titers of HPV 18 L1 VLP-specific serum antibodies in immunized mice induced by administration of the mixture of said five genotypes of HPV L1 VLPs (16, 18, 58, 6 and 11), the mixture of three genotypes of HPV L1 VLPs (16, 18 and 58) and HPV 18 L1 VLP. Arrows indicate three immunization time points.

FIG. 26 is a graph depicting the titers of HPV 58 L1 VLP-specific serum antibodies in immunized mice induced by administration of the mixture of said five genotypes of HPV L1 VLPs (16, 18, 58, 6 and 11), the mixture of three genotypes of HPV L1 VLPs (16, 18 and 58) and HPV 58 L1 VLP. Arrows indicate three immunization time points.

FIG. 27 is a graph depicting the titers of HPV 6 L1 VLP-specific serum antibodies in immunized mice induced by administration of the mixture of said five genotypes of HPV L1 VLPs (16, 18, 58, 6 and 11), the mixture of two genotypes of HPV L1 VLPs (6,11) and HPV 6 L1 VLP. Arrows indicate three immunization time points.

FIG. 28 is a graph depicting the titers of HPV 11 L1 VLP-specific serum antibodies in immunized mice induced by administration of the mixture of the five genotypes of HPV L1 VLPs (16, 18, 58, 6 and 11), the mixture of two genotypes of HPV L1 VLPs (6,11) and HPV 11 L1 VLP. Arrows indicate three immunization time points.

The present invention will be described in detail according to the figures and embodiments. The following embodiments are intended for the purpose of illustration only and are not intended to limit the generality of the methods, compositions, and protocols as herein described. Those skilled in the art are susceptible to include variations and modifications other than those specifically described herein in the present invention. It is understood that all such variations and modifications would fall within the spirit and scope of the present invention.

DETAILED DESCRIPTION OF THE EMBODIMENTS

The present invention relates to a method of optimally modifying the L1 genes, comprising five modifications for increasing transcription stop efficiency and enhancing protein yield, including (1) adjusting gene codons so that they are suitable for expressing the system's codon usage bias; (2) locally adjusting gene codons to remove hypothetical transcription stop codons (such as AT rich structures TATATA, TAGATA, and TACATA etc.), and enhance gene transcription efficiency; (3) locally adjusting gene codons to remove hypothetical splicing donor sites and receiving sites (such as GGTRAG-like splice donors and C/T-rich splicing receivers); (4) locally adjusting gene codons to remove long stems formed by GC rich pairs in mRNA (remove the GC pair portion that is longer than 6), simplifying the complexity of the secondary structure of mRNA to make the conformation loose at the translation starting site, and make it located at an easily accessed loop area (5) locally adjusting the gene codons to change the local conformation around the stop codons (mainly the 1-3 nucleotides downstream of the stop codon). The optimally modified L1 genes in the present invention may produce high expression level of the encoded L1 proteins in insect cells and such L1 proteins may be self-assembled into VLPs. The optimal gene modification method described herein includes a combination of all five modifications, or combinations of any one or more of said five modifications. Said optimal gene modification method for enhancing gene expression in the present invention also contains the use of modifying minor capsid protein L2 gene and early genes E1, E5, E6, E7 or their gene fragments with immune activity.

Preferably, modification of HPV 16 L1 gene is conducted by using a strategy of applying the insect cell codon usage bias and simplifying the complexity of the secondary structure of mRNA to make the conformation loose at the translation starting site, and make it located at an easily accessed loop area. Preferably, modification of HPV 58 L1 gene is conducted by a strategy of applying the combination of all five modifications described herein; modification of HPV 18 L1 gene is conducted by a strategy of applying the combination of all five modifications described herein; modification of HPV 6 L1 gene is conducted by a strategy of applying the combination of all five modifications described herein; modification of HPV 11 L1 gene is conducted by a strategy of applying the combination of all five modifications described herein.

The present invention also relates to the expression of five genotypes of modified HPV L1 genes described herein in insect cells, including transforming E. coli DH10Bac competent cells with each of the pFastBacI plasmid vectors containing said optimally modified HPV L1 genes, obtaining recombinant Bacmids containing each of said optimally modified genes, transfecting insect cells to produce L1 proteins and VLPs, and purifying the L1 VLPs. The present invention also relates to using said optimally modified HPV L1 genes in insect cells to produce L1/L2 VLP or VLPs composed by L1 functional derivatives and L2 functional derivatives. The procedure of producing five genotypes of VLPs involved in the present invention is described below:

Transform E. coli DH10Bac competent cells with pFastBacI-HPV 16 L1M, pFastBacI-HPV 58 L1M, pFastBacI-HPV 18 L1M, pFastBacI-HPV 6 L1M and pFastBacI-HPV 11 L1M recombinant plasmid constructs, respectively;

Select and characterize the recombinant Bacmid containing HPV 16 L1M, HPV 58 L1M, HPV 18 L1M, HPV 6 L1M and HPV 11 L1M genes, respectively;

Transfect logarithmic phase insect cells with the recombinant Bacmid, harvest the supernatant, and obtain the recombinant baculoviruses containing the HPV 16 L1M, HPV 58 L1M, HPV 18 L1M, HPV 6 L1M and HPV 11 L1M genes, respectively;

Infect logarithmic phase Sf9 insect cells with the recombinant baculoviruses containing the HPV 16 L1M, HPV 58 L1M, HPV 18 L1M, HPV 6 L1M and HPV 11 L1M genes, respectively, so that the recombinant baculoviruses may express the introduced HPV 16 L1, HPV 58 L1, HPV 18 L1, HPV 6 L1 and HPV 11 L1 proteins in transfected cells, respectively;

Lyse the insect cells infected with the recombinant baculoviruses containing the HPV 16 L1M, HPV 58 L1M, HPV 18 L1M, HPV 6 L1M and HPV 11 L1M genes, respectively, purify and obtain the HPV 16 L1 VLP, HPV 58 L1 VLP, HPV 18 L1 VLP, HPV 6 L1 VLP and HPV 11 L1 VLP. The present invention relates to the recombinant E. coli DH10Bac strain carrying the recombinant Bacmids which contain the modified HPV16 L1M, HPV 58 L1M, HPV 18 L1M, HPV 6 L1M and HPV 11 L1M genes, respectively. The present invention relates to the Sf9 insect cells carrying said recombinant baculoviruses. The cells involved in the present invention for producing said VLPs is the Sf9 insect cell.

The term "functional L1 protein derivatives" means such derivatives have the ability to induce immune response (if needed, can be used in combination with adjuvant). Said immune response may recognize VLPs composed of full-length L1 protein and/or L1 derivatives. The L1 derivatives may also be fusion proteins, such as those composed of L1 protein and certain early viral protein or L2 protein immunogenic fragment. VLPs in the present invention may be produced by full length HPV L1 protein or specific L1 protein derivatives using standard protocol in the art, as described in a published patent application CN 1498963A (the contents of which is incorporated herein by reference).

The present invention also relates to a modified anti-HPV infection vaccine, said vaccine relates to combinations of various genotypes of VLPs generated from HPV 16, HPV 58, HPV 18, HPV 6 and HPV 11 L1 proteins or functional derivatives thereof. The preferred VLP is L1 VLP of each HPV genotype of the five genotypes described herein. Selectively, and most preferably, said vaccine contains a VLP generated from an additional genotype of the HPV L1 protein and/or L1 derivatives, forming hexavalent vaccines. Such additional genotype may be one of HPV 31, 33, 35, 39, 45, 51, 52, 56, 59, 68, 73, 82, 40, 42, 43, 44, 54, 61, 70, 72, 81, CP6108, 34, 57, 83, 26, 53, 66. When such hexavalent vaccine is used in East Asian countries, said sixth genotype is HPV 52 or HPV 53. Similarly, the present invention may be extended to include two or more additional HPV VLPs genotypes to provide heptavalent and multivalent vaccines. The most preferred HPV genotype of the seventh VLP is HPV 45 or HPV 31.

The vaccine developed in the present invention may be used to prevent or treat HPV-infection and infection associated diseases, such as genital warts, cervical hyperplasia and cervical cancer; any of the vaccines in the present invention can be formulated with VLPs that specifically targeting the protection of genital warts, such as formulated with HPV 6 VLP and/or HPV 11 VLP; or can be formulated with VLPs that specifically targeting protection of cervical cancer, such as formulated with HPV 16 VLP and/or HPV 58 VLP and/or HPV 18 VLP. Preferably, the vaccine is formulated by HPV 16, 58, 18, 6 and 11 VLPs; the preferred compositions include combinations of any one or more of the genotypes of HPV 16, 58, 18, 6 and 11 VLPs. According to the high-occurring diseases caused by infections of certain types of HPVs in East Asian regions, the inventors have been focusing on developing vaccines suitable for such types of diseases. Said vaccines comprise compositions specifically containing HPV 58 VLP.

Preferably, said VLPs only contain the L1 protein or derivatives hereof, and may also be VLPs containing combination of two genotypes of the L1 proteins.

The present invention also include the combined usage of VLPs produced by modified HPV 16, 58, 18, 6 and 11 L1 genes, and other proteins/peptides used in any formats. For example, such (combined usage) may include the proteins/peptides within the VLPs or formulating the proteins/peptides and VLPs into compounds in the applications of drug manufacturing, drug combinations, and particularly in the field of immunotherapy. The present invention also comprise the use in vaccine investigation with VLPs produced by modified HPV 16 L1, HPV 58 L1, HPV 18 L1, HPV 6 L1 and HPV 11 L1 genes as DNA vaccines or other formats.

EXAMPLE 1

Optimized Modifications of HPV 16, 58, 18, 6 and 11 Major Capsid Protein L1 Genes HPV 16, 58, 18, 6 and 11 L1 proteins can be expressed in insect cells by corresponding wild type L1 genes, however, since the expression level of the wild type HPV L1 genes is relatively low, several optimized gene modifications, including codon optimizations, were carried out to increase the HPV L1 protein yield. The modified genes were named L1Ms, and were synthesized in full-length by Shanghai Sangon Biological Engineering Technology & Services Co. Ltd, China. The insect cell codon usage bias is described in the "codon usage database" (Kazusa DNA). When removing hypothetical splicing donor and receiver regions (such as GGTRAG-like splice donors and C/T-rich splicing receivers), removing hypothetical stop signals (such as the AT rich structures TATATA, TAGATA, and TACATA etc.), removing hnRNP-H binding sites, removing long stems formed by GC pairs in RNA secondary structure and reducing the length of C/T-rich tracts (see National Cancer Institute), amino acid codon adjustments of gene sequences should be made locally and manually without changing the encoded amino acids. When simplifying the complexity of the starting area of the secondary structure of mRNA to make it located at an easily accessed loop area, amino acid codon adjustments of gene sequences should also be made locally and manually without changing the encoded amino acids.

SEQ ID NO: 1 demonstrates HPV 16 L1M gene sequence modified by codon usage bias and simplifying the complexity of the starting area of the secondary structure of mRNA to make it located at an easily accessed loop area. The first 129 nucleotides at the N-terminus were modified in HPV 16 L1M, in where 40 nucleotide changes was introduced compare to the wild type HPV 16 L1 gene. The HPV 16 L1M gene is 1518 bp in length and the protein translated from said gene retained same amino acid sequence compare with the wild type. FIG. 1 shows nucleotide sequence alignment between HPV 16 L1M and HPV 16 L1wt.

Compared with wild type HPV 58 L1 sequence, HPV 58 L1M has a 25 amino acids truncation the C-terminus; and has 558 nucleotides change. SEQ ID NO: 2 demonstrates the HPV 58 L1M gene sequence. The HPV 58 L1M is 1423 bp in length, and the protein translated from said gene retained same amino acid sequence compare with the wild type (excluding the truncated region at the C-terminus). FIG. 2 shows nucleotide sequence alignment between HPV 58 L1M and HPV 58 L1wt.

Compared with wild type HPV 18 L1 gene, HPV 18 L1M has a 32 amino acids truncation the C-terminus; and has 566 nucleotides change. SEQ ID NO: 3 demonstrates the HPV 18 L1M gene sequence. The HPV 18 L1M is 1425 bp in length, and the protein translated from said gene retained same amino acid sequence compare with the wild type (excluding the truncated region at the C-terminus). FIG. 3 shows nucleotide sequence alignment between HPV 18 L1M and HPV 58 L1wt.

Compared with wild type HPV 6 L1 gene, HPV 6 L1M has 493 nucleotides change. SEQ ID NO: 4 demonstrates the HPV 6 L1M gene sequence. The HPV 6 L1M is 1504 bp in length, and the protein translated from said gene retained same amino acid sequence compare with the wild type. FIG. 4 shows nucleotide sequence alignment between HPV 6 L1M and HPV 6 L1wt.

Compared with wild type HPV 11 L1 gene, HPV 11 L1M has 601 nucleotides change. SEQ ID NO: 5 demonstrates the HPV 11 L1M gene sequence. The HPV 11 L1M is 1507 bp in length, and the protein translated from said gene retained same amino acid sequence compare with the wild type. FIG. 5 shows nucleotide sequence alignment between HPV 11 L1M and HPV 11 L1wt.

All types of the optimized modified L1M genes (except HPV 16 L1M) were synthesized by Shanghai Sangon Biological Engineering Technology & Services Co. Lid, China, using a well-known gene synthesis method in the art, such as the protocol described in an international patent application WO2005/047315 A2.

EXAMPLE 2

Construction of pFastBacI-HPV 16 L1M, pFastBacI-HPV 58 L1M, pFastBacI-HPV 18 L1M, pFastBacI-HPV 6 L1M and pFastBacI-HPV 11 L1M Recombinant Plasmids Upstream and downstream primers containing appropriate restriction sites for amplifying the corresponding L1M genes were designed using standard protocol, based on gene sequences described in Example 1. Corresponding fragments were amplified by PCR and subcloned into pFastBacI vectors at the corresponding multicloning sites. Corresponding recombinant plasmids were obtained and verified by restriction digestion and sequencing.

Construction of the Modified Human Papillomavirus 16 Major Capsid Protein L1 Gene Given that inhibitory elements exist at the 5 prime end of the wild type HPV 16 L1 gene, such inhibitory elements were inactivated in order to increase the expression level of HPV 16 L1 protein. The modified HPV 16 L1 gene was named HPV 16 L1M.

PCR was conducted using pGEM-T-HPV 16 L1 wt recombinant plasmid as template and pfu DNA polymerase with the forward mutation primer 1 (5'-CCACGCTGGTACCTC-CCGCCTGCTGGCAGTTGGACATCCCTATTTTCC-3') and reverse primer (5'-CCCAAGCIIITACAGCT-TACGTTTTTTGCGTTTAGCAG-3'). The PCR condition was: 30 cycles of denaturation at 94° C. for 60 s, annealing at 61° C. for 60 s, extension at 72° C. for 120 s, and a final extension at 72° C. for 300 s. PCR products were separated by 1% agarose gel electrophoresis and an approximately 1.4 kb specifically amplified fragment was observed. Next, purified fragment (approximately 50 ng) from agarose gel was used as template in another round of PCR reaction, with the pfu DNA polymerase, forward mutation primer 2 (5'-GTGTCCAC-CGACGAGTACGTGGCTCGCACCAACATC-TACTACCACGCTGGTACCTCCCG-3') and reverse primer (5'-CCCAAGCTTTTACAGCT-TACGTTTTTTGCGTTTAGCAG-3'). The PCR condition was: 30 cycles of denaturation at 94° C. for 60 s, annealing at 62° C. for 60 s, extension at 72° C. for 120 s, and a final extension at 72° C. for 300 s. PCR products were separated by 1% agarose gel electrophoresis and an approximately 1.45 kb specifically amplified fragment was observed. Next, purified fragment (approximately 50 ng) from agarose gel was used as template in another round of PCR reaction, with the pfu DNA polymerase, forward mutation primer 3 (5'-AGGCCACCGT-GTACCTGCCCCCCGTGCCCGTGTCCAAG-GTGGTGTCCACCGACGAGTAC-3') and reverse primer (5'-CCCAAGCTTTTACAGCT-TACGTTTTTTGCGTTTAGCAG-3'). The PCR condition was: 30 cycles of denaturation at 94° C. for 60 s, annealing at 61° C. for 60 s, extension at 72° C. for 120 s, and a final extension at 72° C. for 300 s. PCR products were separated by 1% agarose gel electrophoresis and an approximately 1.5 kb specifically amplified fragment was observed. Next, purified fragment (approximately 50 ng) from agarose gel was used as template in another round of PCR reaction, with the pfu DNA polymerase, forward mutation primer 4 (5'-CTAGTCTA-GAGCCGCCACCATGTCCCTGTGGCTGC-CCTCCGAGGCCACCGTGTACCTGC-3') and reverse primer (5'-CCCAAGCIIITACAGCTTACGTTTTTT-GCGTTTAGCAG-3'). The PCR condition was: 30 cycles of denaturation at 94° C. for 60 s, annealing at 61° C. for 60 s, extension at 72° C. for 120 s, and a final extension at 72° C. for 300 s. PCR products were separated by 1% agarose gel electrophoresis and an approximately 1.5 kb specifically amplified fragment was observed. Said fragment was purified. Both of the forward mutation primer 4 and reverse primer contained Xba I and Hind III sites, and said two enzymes were used to digest the purified fragment to produce a final PCR product. The recovered PCR fragment and a baclouvirus-insect cell expression vector pFastBacI (Invitrogen Corp.) restriction digestion product were quantified and mixed at a molar ratio of 4:1, and ligated at 16° C. overnight using T4 DNA ligase. The ligation product was then used to transform DH5α competent cells and recombinant colonies were selected and verified by PCR. Positive clones were mini-preped and digested by Xba I and Hind III to obtain fragment the size of 1.5 kb, which is consistent with that of the HPV 16 L1M. Stock was kept for the positive clones and the DNA fragment was sent to Invitrogen for sequencing using the Applied Biosystem sequencing method. Sequencing result showed that the modified mutation was correctly constructed, having identical sequence to that of the SEQ IN NO: 1. Compare with the HPV 16 L1wt gene, the first 129 bp of HPV 16 L1M was mutagenesized by homologous recombination, and contains 13 nucleotide difference compared with the modified sequence reported by Collier B et al. (Collier B, et al. J Virol. 2002, 76:2739-2752; Rollman E, et al. Virology. 2004, 322:182-189), which has 514 bp (homologous recombination) at the N-terminus. The difference is mainly caused by the different selections of codons that compose amino acids of Ser, Ala, Arg and Gly; In addition, the HPV 16 L1 mRNA translation starting site in the study reported by Collier B et al. was located at the stem region outside the expanded loop, while the translation starting site of HPV 16 L1M mRNA in the present patent was located at the opening region outside the expanded loop, which resulted in a simpler secondary structure of the HPV 16 L1M mRNA and an easy access for the RNA polymerase. Comparing with the above described prior art, the present invention provides increased transcription and expression and produces the HPV 16 L1M recombinant plasmid.

2. Construction of Other Types of the PFastBacI Recombinant Plasmids

Similar method as described above for HPV 18 L1M recombinant cloning was used to construct other HPV types of recombinant pFastBacI plasmids. Detailed description is as follows: primers were designed based on HPV 18 L1M gene sequence. Forward primer was 5'-GGGAATTCGC-CGCCCACCATGGCTCTCTGGAGACCCTCC-3' and reverse primer was 5'-CGCTCTAGAATTAGAGACCCGC-CTGGACGAG-3'. The forward primers contained an EcoR I restriction site and a Kozak sequence GCCGCCACC. The reverse primer contained an Xba I restriction site and a stop codon. PCR reaction was performed using pGEM-T-HPV 18 L1M plasmid as template and pfu DNA polymerase as the enzyme. The PCR condition was: 25 cycles of denaturation at 94° C. for 60 s, annealing at 68° C. for 60 s, extension at 72° C. for 120 s, and a final extension at 72° C. for 300 s. PCR products were separated by 1% agarose gel electrophoresis and an approximately 1.42 kb specifically amplified fragment was observed. Such PCR fragment was purified and digested by EcoR I and Xba I to produce a final PCR product. Said PCR fragment was recovered from gel and quantified. The pFastBac I vector was also treated with same restriction enzymes and the digestion product was recovered and quantified. The above prepared PCR fragment and pFastBac I vector were mixed at a molar ratio of 4:1, and ligated at 16° C. overnight using T4 DNA ligase. The ligation product was then used to transform DH5α competent cells and the white, recombinant colonies were selected and verified by PCR. Positive clones were minipreped and digested by Ecor I and Xba I to obtain fragment with a size of 1.42 kb, which is consistent with that of the HPV 18 L1M. The DNA fragment was sent to Invitrogen Crop. for sequencing using the Applied Biosystem sequencing method. Sequencing result showed that the modified mutation was correctly constructed, having identical sequence to that of the HPV 18 L1M.

E. coli DH10Bac competent cells were transformed with each recombinant pFastBacI plamid described above (pFastBacI-HPV 16 L1M, pFastBacI-HPV 58 L1M, pFastBacI-HPV 18 L1M, pFastBacI-HPV 6 L1M and pFastBacI-HPV 11 L1M, respectively), and obtained recombinant Bacmids. Recombinant baculovirus was generated by transfecting Sf9 insect cells with each purified recombinant Bacmid. The protocol of using recombinant baculoviruses to transfect insect cells for producing L1 protein and L1 VLPs is well-known (such as the protocols used in Chinese patent applications CN 1498963A and 200510009717).

EXAMPLE 3

Protein Expression Analysis of Modified HPV L1 Genes (by SDS-PAGE with Coomassie Blue Staining or Western Blot)

5 μg insect cell lysates transfected by each of the recombinant baculoviruses described in Example 2 was collected at 72 h post-infection, denatured at 70° C. for 5 min with final concentration of 10 mmol/L DTT, and separated by 8% SDS-PAGE. The SDS-PAGE gel was then stained with Coomassie blue R-250 at room temperature for 2 h, and destained for several hours until the bands become clearly visible.

0.5 μg insect cell lysates transfected by each of the recombinant baculoviruses was harvested at 72 h post-infection, denatured at 70° C. for 5 min with final concentration of 10 mmol/L DTT, and separated by 8% SDS-PAGE. The proteins were transferred onto membranes and blocked in 5% BSA at room temperature for 2 h. Primary antibody was added and incubated. After washing the cells, goat anti-rabbit and goat anti-mouse HRP secondary antibodies were added at 1:5000, and incubated for 1 h at room temperature. After extensive washing, (the membrane) was incubated for 5 min at room temperature with a chemical luminescence amplification substrate (PIERCE, Catalog No. 34079), and (the result) was developed onto film in the darkroom.

The results showed that HPV 16 L1M, HPV 58 L1M, HPV 18 L1M, HPV 6 L1M and HPV 11 L1M genes have specifically expressed their corresponding proteins, and the expression levels of HPV L1M genes were significantly increased compare with their wild type counterparts.

The protein expression level of HPV 16 L1M gene was increased by 1.68 times. As shown in FIG. 13, Sf9 cells were infected with recombinant HPV 16 L1wt and modified HPV 16 L1 baculoviruses. Cell lysates were harvested 72 h post-infection and analyzed by Western blot. A housekeeping gene for baculoviruses, lef-7, was used as an internal control. Anti-HPV 16 L1 conservative liner epitope Camvir-1 monoclonal antibody and rabbit anti-lef-7 antiserum were used to detect the HPV 16 L1 and the lef-7 proteins, respectively. The bands in Lane 1 represent the expression level of modified HPV 16 L1, while bands in Lane 2 represent the expression level of HPV 16 L1wt. The Optical Density (OD) value of modified L1gene divided by OD value of the corresponding Lef-7 and the OD value of the HPV 16 L1wt gene divided by OD value of corresponding Lef-7 were compared, and the result indicated that the expression level of HPV 16 L1M gene was approximately 1.68 times as high as that of the HPV 16 L1wt gene. As shown in FIG. 16, the purified HPV 16 L1 protein may be self-assembled into uniform virus-like particles with diameter of 50 nm.

The protein expression level of HPV 58 L1M gene was increased by 1.82 times. As shown in FIG. 14, Sf9 cells were infected with recombinant HPV 58 L1wt and modified HPV 58 L1 baculoviruses. Cell lysates were harvested 72 h post-infection and analyzed by Western blot. A housekeeping gene for baculoviruses, lef-7, was used as an internal control. Anti-HPV 58 L1 conservative liner epitope Camvir-1 monoclonal antibody and rabbit anti-lef-7 antiserum were used to detect HPV 58 L1 and lef-7 proteins, respectively. The bands in Lane 1 represent the expression level of modified HPV 58 L1, while bands in Lane 2 represent the expression level of HPV 58 L1wt. The Optical Density (OD) value of modified L1 gene divided by OD value of the corresponding Lef-7 and the OD value of the HPV 58 L1wt gene divided by OD value of corresponding Lef-7 were compared, and the result indicated that the expression level of HPV 58 L1M gene was approximately 1.82 times as high as that of the HPV 58 L1wt gene. As shown in FIG. 17, the purified HPV 58 L1 protein may be self-assembled into uniform virus-like particles with diameter of 50 nm.

The protein expression level of HPV 18 L1M gene was increased by 1.29 times. As shown in FIG. 15, Sf9 cells were infected with recombinant HPV 18 L1wt and modified HPV 18 L1 baculoviruses. Cell lysates were harvested 72 h post-infection and analyzed by Western blot. A housekeeping gene for baculoviruses, lef-7, was used as an internal control. Anti-HPV 18 L1 conservative liner epitope Camvir-1 monoclonal antibody and rabbit anti-lef-7 antiserum were used to detect HPV 18 L1 and lef-7 proteins, respectively. The bands in Lane 1 represent the expression level of modified HPV 18 L1, while the bands in Lane 2 represent the expression level of HPV 18 L1wt. The Optical Density (OD) value of modified L1 gene divided by OD value of the corresponding Lef-7 and the OD value of the HPV 18 L1wt gene divided by OD value of corresponding Lef-7 were compared, and the result indicated that the expression level of HPV 18 L1M gene was approximately 1.29 times as high as that of the HPV 18 L1wt gene. As shown in FIG. 18, the purified HPV 18 L1 protein may be self-assembled into uniform virus-like particles with diameter of 50 nm.

The protein expression level of HPV 11 L1M gene was increased by 1.56 times. As shown in FIG. 11, Sf9 cells were infected with recombinant HPV 11 L1wt and modified HPV 11 L1 baculoviruses. Cell lysates were harvested 72 h post-infection and analyzed by Western blot. A housekeeping gene for baculoviruses, lef-7, was used as an internal control. Anti-HPV 11 L1 conservative liner epitope Camvir-1 monoclonal antibody and rabbit anti-lef-7 antiserum were used to detect HPV 11 L1 and lef-7 proteins, respectively. The bands in Lane 1 represent the expression level of modified HPV 11 L1, while the bands in Lane 2 represent the expression level of HPV 11 L1wt. The Optical Density (OD) value of modified L1 gene divided by OD value of the corresponding Lef-7 and the OD value of the HPV 11 L1wt gene divided by OD value of corresponding Lef-7 were compared, and the result indicated that the expression level of HPV 11 L1M gene was approximately 1.56 times as high as that of the HPV 11 L1wt gene. As shown in Example 4, FIG. 20, the purified HPV 11 L1 protein may be self-assembled into uniform virus-like particles with diameter of 50 nm.

The protein expression level of HPV 6 L1M gene was increased by 1.60 times. As shown in FIG. 12, Sf9 cells were infected with recombinant HPV 6 L1wt and modified HPV 6 L1 baculoviruses. Cell lysates were harvested 72 h post-infection and analyzed by Western blot. A housekeeping gene for baculoviruses, lef-7, was used as an internal control. Anti-HPV 6 L1 conservative liner epitope Camvir-1 monoclonal antibody and rabbit anti-lef-7 antiserum were used to detect HPV 6 L1 and lef-7 proteins, respectively. The bands in Lane 1 represent the expression level of modified HPV 6 L1, while the bands in Lane 2 represent the expression level of HPV 6 L1wt. The Optical Density (OD) value of modified L1 gene divided by OD value of the corresponding Lef-7 and the OD value of the HPV 6 L1wt gene divided by OD value of corresponding Lef-7 were compared, and the result indicated that the expression level of HPV 6 L1M gene was approximately 1.60 times as high as that of the HPV 6 L1wt gene. As shown in Example 4, FIG. 19, the purified HPV 6 L1 protein may be self-assembled into uniform virus-like particles with diameter of 50 nm.

EXAMPLE 4

Purification of the HPV 16, 58, 18, 6 and 11 L1 VLPs and Transmission Electron Microscopy Assay Samples were kept in 50 ml centrifuge tubes on ice and lysed by using a Fisher 550 ultrasonic machine at speed 4.5 with 25 sec sonication at 20 sec intervals for 5 min. The extract was centrifuged at 10,000 rpm at 4° C. for 15 min and the supernatant was collected. 8 ml of CsCl was first added in a Beckman centrifuge tube, and then 8 ml of 40% sucrose was slowly added on top of CsCl to form a clear interphase between CsCl and sucrose. The 21 ml supernatant containing VLP was layered on the CsCl/sucrose gradient and centrifuged at 27,000 rpm at 10° C. for 2.5 h. The supernatant was collected with a pepitor until reaching the cloud-like sucrose/CsCl interphase. Said supernatant was transferred to a centrifuge tube using a 10 ml syringe, and filled up with extraction buffer for balancing the centrifuge tubes. The samples were centrifuged at 50,000 rpm at 20° C. for 16 h. After centrifugation, there was a visible cloud-like region of VLP bands. The VLP bands were fractionated and collected by puncturing tubes at the bottom, and each fraction was analyzed by Western blot. The positive VLP containing fractions were collected and dialyzed against 10 mM HEPES (pH 7.2) at 4° C. for 2-6 hours. The samples were placed onto nitrocellulose carbon grids for 1 minute and washed with water. The grids were stained with 1% uranyl acetate for 30 seconds. Excess staining solution was removed by filer paper and the grids were left air-dry. Specimens were examined and photographed with a JEM1010 electron microscope at 50,000× magnification. As shown in FIG. 16-20, HPV 16, 58, 18, 6 and 11 L1 VLPs were regular shaped particles with a diameter of 55 nm.

After purification by dialysis, the L1 VLP was quantified using a bicinchoninic acid (BCA) kit (PIERCE). 1 L of $2-2.5 \times 10^6$/ml Sf9 insect cells infected by each of the baculovirus expression systems yielded 8 mg of HPV 16 VLP, 7.5 mg of HPV 58 VLP, 7.9 mg of HPV 18 VLP, 8.5 mg of HPV 6 VLP and 10 mg of HPV 11 VLPs, respectively.

EXAMPLE 5

Hemagglutination Assay of HPV 16, 58, 18, 6 and 11 L1 VLPs

The protocol of using L1 VLPs produced by the optimally modified HPV 16, 58, 18, 6 and 11 L1 genes to induce hemagglutination is as follows: blood from mice carotid artery was collected and placed into EP tubes containing 109 mM citrate chloride (m/v). The tubes were centrifuged at 4° C. for 5 min, and supernatant was discarded. Erythrocytes were washed three times with PBS containing BSA (1 mg/ml), and were re-suspended at a final concentration of 1% (v/v). HPV 16, 58, 18, 6 and 11 L1 VLPs were dialyzed against 10 mM HEPES (pH 7.2) and the concentrations of each HPV L1 VLP were adjusted to 4 ng/µl with PBS containing BSA (1 mg/ml). In a 96-well U-bottomed plate, 50 µl of 4 ng/µl each of the HPV L1 VLPs was added into the first well, and a two-fold serial dilution was made with PBS containing BSA (1 mg/ml) for 10 continues times. 50 µl of 1%

(v/v) erythrocyte was added to each well, and the mixture of VLPs and erythrocyte was incubated at 4° C. for 3 hours. The plate was later photographed.

HPV 16, 58, 18, 6 and 11 L1 VLP effectively hemagglutinated mouse erythrocytes. The minimal concentration of HPV 16, 58, 18, 6 and 11 L1 VLP to hemagglutinate mouse erythrocytes is 3.12 ng/100 μl; 3.12 ng/100 μl; 3.12 ng/100 μl; 3.12 ng/100 μl and 6.25 ng/100 μl, respectively. FIG. 21 shows the representing result of the hemagglutination assay of HPV 16 L1 VLP. Similar results were observed with other genotypes of HPV L1 VLPs.

EXAMPLE 6

Examination of the Conformation-Dependent Serum Neutralizing Antibodies Induced by HPV L1 VLP VLPs produced by wild type HPV 16, 58, 18, 6 or 11 L1 genes and a denatured (100° C. for 5 min) HPV 16 L1 VLP were diluted with PBS to a concentration of 0.2 μg/100 μl. In a 96 well ELISA plate, 100 μl of 0.2 μg/100 μl said native or denatured L1 VLPs was added to a well so that the wells were coated, and incubated at 4° C. for overnight. The wells were washed for 3 times with 0.05% PBST, blocked with 5% BSA-0.05% PBST, and then incubated with the 1:3000 diluted mouse anti-sera from each genotype at room temperature for 2 h. The wells were washed again for 3 times with 0.05% PBST and incubated with peroxidase-conjugated goat anti-mouse secondary IgG at 1:3000 dilution at 37° C. for 1 h. After 5 times extensive washing, 100 μl orthophenylenediamine (OPD) substrates was added to the wells and incubated at 37° C. for 5 min (in dark). The reaction was stopped by adding 2M $H_2SO_4$ and the optical density (OD) value was measured with an automated ELISA microplate reader at the wavelength of 490 nm.

As shown in FIG. 22, the neutralizing antibodies induced by the L1 VLPs that were produced by modified HPV 16, 58, 18, 6 or 11 L1 genes were conformation-dependent and efficiently bound to the native L1 VLPs, but not to the denatured L1 VLPs.

EXAMPLE 7

Splenocytes Proliferation Assay of HPV VLPs in Immunized Mice

Splenocytes were isolated from mice immunized with L1 VLPs produced by the modified HPV 16, 58, 18, 6 and 11 L1 genes three weeks post the third immunization. The experiment was performed in a 96-well U-bottomed plate: $3 \times 10^5$ splenocytes/200 μl/well was added to each well. 2 μg L1 VLPs produced by wild type HPV 16, 58, 18, 6 or 11 L1 genes was added to the stimulated wells, while no L1 VLPs were added to the control wells. Each treatment was performed in triplicate. The plate was incubated at 37° C. for 72 h and complete medium containing 1 μCi of $^3$H-TdR was added to each well to mix, and incubated for another 18 h. The cells were harvested by a multiple-porus cell collector and laid onto a glass fiber membrane for air dry. The cells were then placed in a scintillation cup of a βplate-reader containing 5 ml scintillation liquid and the value of counts per minute (cpm) was measured. The stimulation index (SI) was calculated as: SI=mean cpm of the stimulated cells/mean cpm of the medium only control cells.

FIG. 23 demonstrates that the splenocytes isolated from mice immunized with L1 VLPs that were produced by the modified HPV 16, 58, 18, 6 and 11 L1 genes effectively proliferated when stimulated by corresponding HPV L1 VLPs. The mean values of SI of HPV 16, 18, 58, 6 and 11 L1 VLPs were 6.040, 5.837, 6.041, 5.706 and 5.557, respectively; and are significantly higher than the PBS control (the mean value of SI was 1.037).

EXAMPLE 8

Immunization of Mice with HPV 16/58/18/6/11 L1 VLPs and Titer Measurement of the Induced Serum Neutralizing Antibodies Immunization of the Mice 4-6 week-old BALB/c mice were randomly divided into 9 groups with 4 mice per group. Mice were administrated intramuscularly with combinations of different genotypes of VLPs at day 0, 13 and 27. The groups were divided as follows:
  1): a PBS control;
  2): a mixed immune group of HPV 16 L1 VLP (5 μg), HPV 58 L1 VLP (5 μg) and HPV 18 L1 VLP (5 μg);
  3): a mixed immune group of HPV 6 L1 VLP (5 μg) and HPV 11 L1 VLP (5 μg);
  4): a mixed immune group of HPV 16 L1 VLP (5 μg), HPV 58 L1 VLP (5 μg), HPV 18 L1 VLP (5 μg), HPV 6 L1 VLP (5 μg) and HPV 11 L1 VLP (5 μg);
  5): a single immune group of HPV 16 L1 VLP (5 μg);
  6): a single immune group of HPV 58 L1 VLP (5 μg);
  7): a single immune group of HPV 18 L1 VLP (5 μg);
  8): a single immune group of HPV 6 L1 VLP (5 μg);
  9): a single immune group of HPV 11 L1 VLP (5 μg).

2. Measurement of the HPV 16/58/18/6/11 L1 VLP-Induced Serum Neutralizing Antibodies Blood was drawn from tail vein at day 0, 14, 28, 42, 56 and 70 (post-immunization). Serum was separated and titers of serum neutralizing antibodies were measured by indirect ELISA. The protocol is as follows: 96-well ELISA plates were coated with 0.1 μg/100 μl of each of the different genotypes of VLPs at 4° C. for overnight. After removing the coating buffer, the wells were washed 3 times with 0.05% PBST. 200 μl 5% BSA in 0.05% PBST was added to each well and blocked at room temperature for 2 h. After removing the blocking buffer, the wells were washed 3 times with PBST. The serum waiting for measuring was diluted at different concentrations and the diluted samples were added to each well at 100 μl per well, incubated at room temperature for 2 h. After removing the samples, the wells were then washed 3 times with 0.05% PBST and incubated with peroxidase-conjugated goat anti-mouse IgG secondary antibody at a 1:3000 dilution at 37° C. for 1 h. After removing the secondary antibody and washing for 5 times, 100 μl orthophenylenediamine (OPD) substrate was added to each well and incubated at 37° C. for 5 min (in dark). The reaction was stopped by adding 50 μl 2M $H_2SO_4$. The optical density (OD) of the samples was recorded with an automated ELISA microplate reader at 490 nm. The antibody titer is defined as: the OD value with reciprocal dilution is at least twice of the background and the absolute OD value is greater than 0.2.

The results are shown in FIG. 24-28. Details are as follows:
  1). HPV 16 L1 VLP-specific immune response: anti-HPV 16 L1 VLP antibodies were induced in groups 2, 4 and 5. Strong immune response was induced after 3 times of immunization, and there was no significant titer difference among the three groups. There was no interference among components;
  2). HPV 18 L1 VLP-specific immune response: anti-HPV 18 L1 VLP antibodies were induced in groups 2, 4 and 7. Strong immune response was induced after 3 times of immunization, and there was no significant titer difference among the three groups. There was no interference among components;

3). HPV 58 L1 VLP-specific immune response: anti-HPV 58 L1 VLP antibodies were induced in groups 2, 4 and 6. Strong immune response was induced after 3 times of immunization, and there was no significant titer difference among the three groups. There was no interference among components;

4). HPV 6 L1 VLP-specific immune response: anti-HPV 6 L1 VLP antibodies were induced in groups 3, 4 and 8. Strong immune response was induced after 3 times of immunization, and there was no significant titer difference among the three groups. There was no interference among components;

5). HPV 11 L1 VLP-specific immune response: anti-HPV 11 L1 VLP antibodies were induced in groups 3, 4 and 9. Strong immune response was induced after 3 times of immunization, and there was no significant titer difference among the three groups. There was no interference among components;

Taken together, the result revealed that when administrated as a composition, no interference was observed when each genotype of the five VLPs (HPV16, 18, 58, 6 and 11 L1 VLPs) was used in combinations.

What is claimed is:

1. An optimally modified HPV 18 L1M gene sequence consisting of the nucleotide sequence shown as SEQ ID NO: 3.

2. A recombinant pFastBacl plasmid containing an optimally modified gene sequence consisting of the nucleotide sequence shown as SEQ ID NO:3.

3. A recombinant Bacmid containing an optimally modified gene sequence consisting of the nucleotide sequence shown as SEQ ID NO:3.

4. A recombinant *E. coli* DH 10Bac strain containing the recombinant Bacmid according to claim 3.

5. A recombinant baculovirus containing an optimally modified gene sequence consisting of the nucleotide sequence shown as SEQ ID NO:3.

6. An insect cell line sf9 infected with the recombinant baculovirus of claim 5.

* * * * *